United States Patent
Tajima et al.

(10) Patent No.: US 6,557,558 B1
(45) Date of Patent: May 6, 2003

(54) MEDICAL TREATMENT APPARATUS

(75) Inventors: Fujio Tajima, Tsuchiura (JP); Masakatsu Fujie, Ushiku (JP); Hiroshi Takeuchi, Matsudo (JP); Etsuji Yamamoto, Akishima (JP); Koichi Sano, Yokohama (JP); Kazutoshi Kan, Chiyoda (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/648,453

(22) Filed: Aug. 28, 2000

(30) Foreign Application Priority Data

Aug. 31, 1999 (JP) .......................... 11-244796

(51) Int. Cl.[7] .............................................. A61B 19/00
(52) U.S. Cl. ...................................................... 128/897
(58) Field of Search ................................ 600/300, 407, 600/417, 102, 427, 429, 160, 408, 411; 128/897, 898; 378/62; 606/130; 324/319

(56) References Cited

U.S. PATENT DOCUMENTS

| | | | |
|---|---|---|---|
| 5,078,140 A | * 1/1992 | Kwoh | 600/417 |
| 5,230,338 A | 7/1993 | Allen et al. | |
| 5,279,309 A | 1/1994 | Taylor et al. | |
| 5,445,166 A | 8/1995 | Taylor | |
| 5,458,125 A | * 10/1995 | Schweikard | 600/407 |
| 5,630,431 A | 5/1997 | Taylor | |
| 5,660,176 A | * 8/1997 | Iliff | 600/300 |
| 5,694,142 A | 12/1997 | Dumoulin et al. | |
| 5,769,092 A | 6/1998 | Williamson, Jr. | |
| 5,799,055 A | 8/1998 | Peshkin et al. | |
| 5,876,325 A | * 3/1999 | Mizuno et al. | 600/102 |
| 5,913,820 A | * 6/1999 | Bladen et al. | 600/407 |
| 5,976,156 A | * 11/1999 | Taylor et al. | 606/130 |
| 5,987,349 A | 11/1999 | Schulz | |
| 6,024,695 A | 2/2000 | Taylor et al. | |
| 6,028,912 A | 2/2000 | Navab | |
| 6,033,415 A | 3/2000 | Mittlstadt et al. | |
| 6,058,323 A | 5/2000 | Lemelson | |
| 6,167,292 A | 12/2000 | Badano et al. | |
| 6,185,445 B1 | 2/2001 | Knüttel | |
| 6,201,394 B1 | 3/2001 | Danby et al. | |
| 6,201,984 B1 | 3/2001 | Funda et al. | |
| 6,205,411 B1 | 3/2001 | DiGioia, III et al. | |
| 6,208,145 B1 | 3/2001 | Danby et al. | |
| 6,233,474 B1 | 5/2001 | Lemelson | |
| 6,246,898 B1 | 6/2001 | Vesely et al. | |
| 6,249,713 B1 | 6/2001 | Geiger et al. | |
| 6,301,495 B1 | 10/2001 | Gueziec et al. | |

FOREIGN PATENT DOCUMENTS

| | | |
|---|---|---|
| EP | 0 391 376 A1 | 10/1990 |
| JP | 8-280710 | 10/1996 |
| WO | WO 98/33451 | 8/1998 |

OTHER PUBLICATIONS

Japanese Patent Unexamined Publication No. 8–280710.

* cited by examiner

Primary Examiner—Max F. Hindenburg
Assistant Examiner—Nikita Veniaminov
(74) Attorney, Agent, or Firm—Antonelli, Terry, Stout & Kraus, LLP

(57) ABSTRACT

A medical treatment apparatus capable of performing exact medical treatment is provided. The medical treatment apparatus includes detection means for detecting the condition of a human body to be treated, medical treatment means for treating said human body, and display means for displaying results of computing by computing means for computing a plan for said medical treatment on the basis of detection results from said detection means.

12 Claims, 19 Drawing Sheets

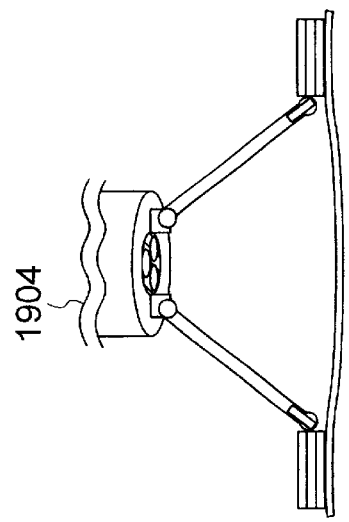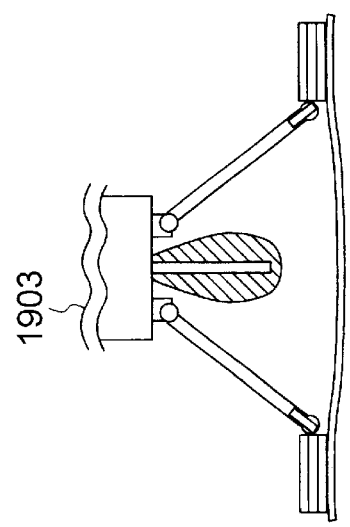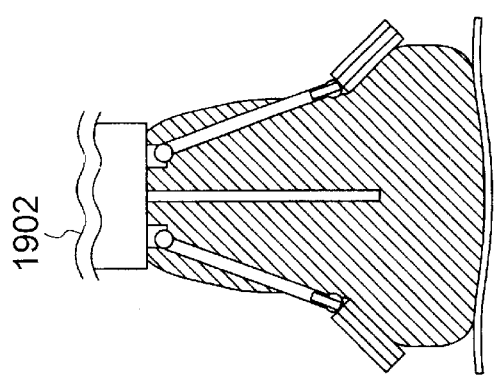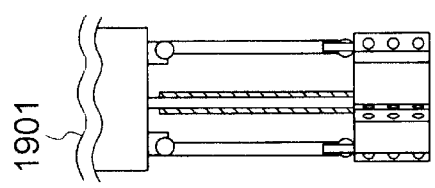

MEDICAL TREATMENT APPARATUS

BACKGROUND OF THE INVENTION

The present invention relates to a medical treatment apparatus that supports medical treatment actions to an affected area of a patient.

In conventional medical treatment, particularly, conventional surgical treatment, after conducting a diagnosis with the aid of information obtained beforehand, in particular, image information obtained by an image measuring apparatus, a medical treatment plan was formed on the basis of results of the diagnosis and medical treatment was performed according to the plan.

On the other hand, in recent years, operators have come to use an ultrasonic scanner, a radioscopic apparatus, etc. as measuring instruments during surgical operations. An example of technique for performing the medical treatment of patients and support of such medical treatment with the aid of information from such measuring instruments is described in JP-A-8-280710. In this conventional technique, an apparatus for displaying information obtained beforehand from a measuring instrument as described above to operators who perform medical treatment is provided.

The above ultrasonic scanner can perform only local measurement and it was difficult to grasp a general structure. Further, there were cases where tomographic images from an arbitrary direction as in MRI and CT could not be taken and hence images in the direction in which an operator wanted to observe them could not be obtained. On the other hand, the radioscopic apparatus was not used to repeatedly take images because the problem of irradiation with radiant rays cannot be neglected.

In the above conventional technique, therefore, the external structure and internal structure of a patient or an affected area are presented in real time, whereas a medical treatment plan is not modified or updated.

For this reason, a medical treatment plan is not sequentially generated, modified or updated with the aid of such image information, and instead an operator performed an surgical operation by forming a judgment in real time during the surgical operation.

However, during actual medical treatment and, in particular, during surgical treatment (hereinafter referred to as an operation or a surgical operation), it is not seldom that the condition of a patient or an affected area undergoes an unexpected change, such as deformation, as the medical treatment proceeds and, therefore, there were cases where it was not necessarily the best to perform an operation according to a plan formed beforehand or an operation could not be performed as planned. It is not difficult to say that in the conventional technique, a change in the condition of a patient or an affected area during an operation was responded to in the best manner like this, and it was not taken into consideration that the lack of this capacity of the conventional technique to respond to a change in the condition of a patient or an affected area during an operation prevents an improvement in operation performance.

Furthermore, trends for the past several years include trying out of a method of calculating a direction of approach in a stereotactic neurosurgery with the aid of an image measuring instrument capable of taking tomographic images near an affected area. However, there are only a few clinical examples and it cannot be said that this method has been put to practical use. Even if this method is carried out by means of an MRI and X-ray CT, instructions based on results of a calculation exceeds the limits of human manual techniques because of the complexity of a path through an object point of operation or because of the fineness (resolution) of work and for other reasons, and it is not seldom that this method may not be implemented.

The complexity of a path can be improved by increasing the size of an incision, i.e., a cut-open portion of a patient. However, an increase in the size of the incision increases the burden on the patient during and after the operation and, therefore, it is undesirable to increase the size of the incision unnecessarily. In medical treatment, it is desirable that the incision be as small as possible in order to minimize damage to the patient and that an operation be performed in a narrow space by looking at movements of the internal organs by means of surgical instruments and also, in many cases, an endscope inserted from the small incision.

On the other hand, an operator must use images from an endscope from which it is difficult to get to know a general structure of the affected area including its surrounding area and is also required to carry out fine and well-done operating manipulation on the object which continues to change in real time while manipulating surgical instruments in a space where movements are limited, with the result that it becomes more and more difficult to exactly update and modify a medical treatment plan during an operation. This point was not taken into consideration in the above conventional technique.

Further, in some portions to be operated, if the dynamic behavior and functions of an organ in question can be measured in the period from incision to immediately before and after the performance of an operation for actual medical treatment, the wound can be prevented from being closed with insufficient medical care, with the result that the performance of the operation is remarkably improved. In the medical treatment of heart disease, for example, if, before and after bypassing, valve replacement, etc., an operator can get to know the patency condition of bypassed blood vessels and the recovery condition of the heart functions by valve replacement, there are many advantages including lowering the probability of a re-operation.

Conventionally, in such operation of heart disease, information on the internal condition of an affected area and patient has been collected through the use of an ultrasonic scanner. Although this measure enables information on dynamic behavior, such as the condition of blood currents and pulses, to be obtained, it cannot grasp a general structure. In some cases, therefore, obtained information is insufficient for medical treatment.

SUMMARY OF THE INVENTION

An object of the invention is to provide a medical treatment apparatus capable of performing more exact medical treatment by presenting a medical treatment plan which is modified during medical treatment to an operator who performs the operation and uses this medical treatment apparatus.

In order to achieve the above object, there is provided in the invention a medical treatment apparatus comprising detection means for detecting the condition of a human body to be treated, medical treatment means for treating the human body, and display means for displaying results of computing with the aid of computing means for computing a plan for the medical treatment on the basis of detection results from the detection means.

BRIEF DESCRIPTION OF THE DRAWINGS

FIGS. 19A to 19D are illustrations of a sequence adopted when a folding stabilizer is caused to be attracted onto an organ in question.

DETAILED DESCRIPTION OF THE PREFERRED EMBODIMENTS

Figure 1:
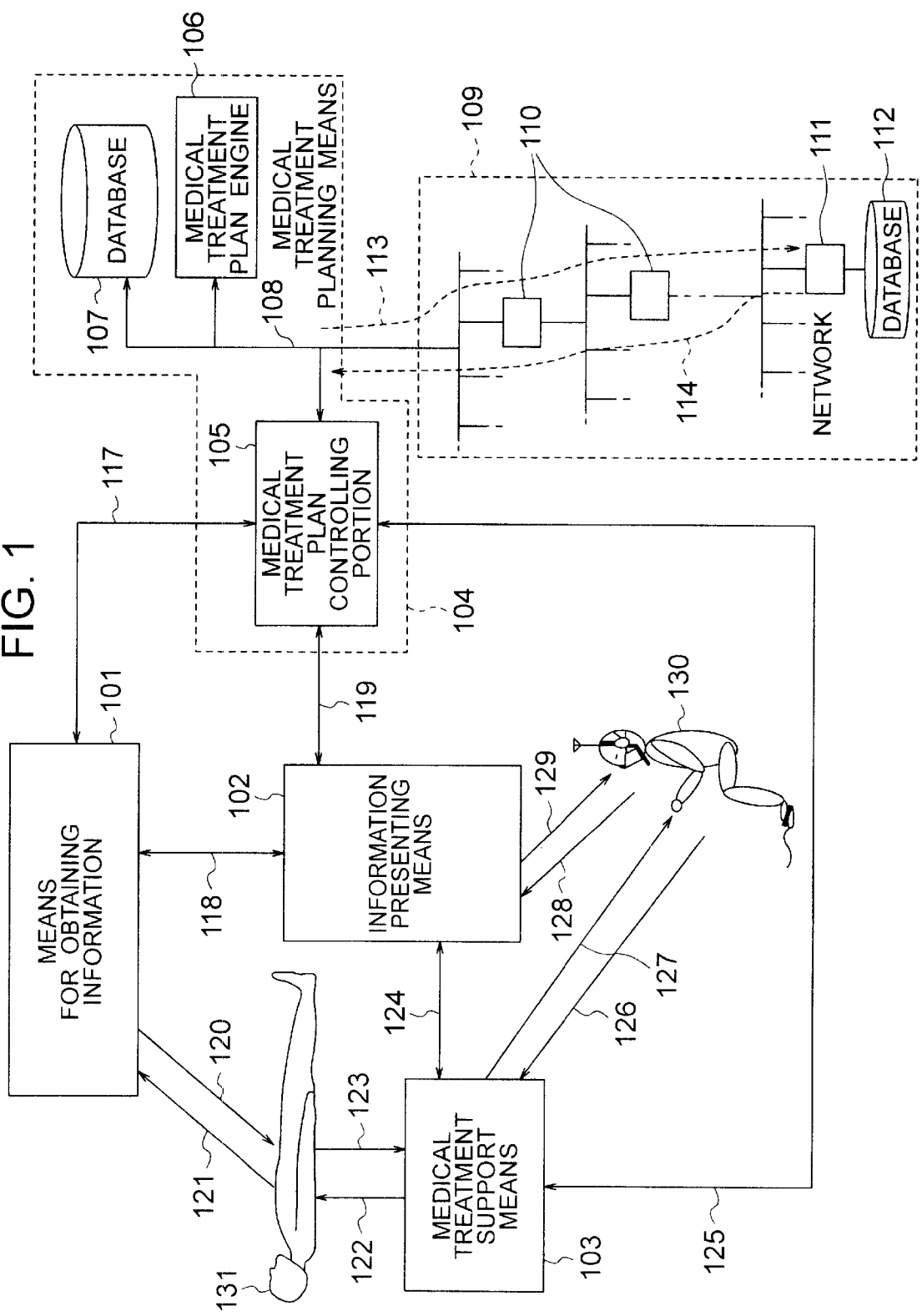
FIG. 1 is a structural view of the invention.

Embodiments of the invention are described below by referring to the drawings.

FIG. 1 shows a general configuration of an embodiment of the invention. In the figure, the numeral 101 denotes measuring means for obtaining information on the condition of an affected area or a patient, the numeral 102 display means for presenting the above obtained information, the numeral 103 medical treatment means for performing medical treatment by directly approaching the patient and affected area, and the numeral 104 medical treatment planning means for computing a medical treatment plan on the basis of the above obtained information and information on the patient and affected area obtained beforehand. In this medical treatment planning means 104, the numeral 106 denotes medical treatment plan computing means for computing a medical treatment plan, and the medical treatment plan computed by this computing means is transmitted to a medical treatment plan controlling portion 105. This medical treatment plan controlling portion 105 sends control instructions to the above medical treatment means 103 on the basis of this medical treatment plan, transmits information on the medical treatment plan to the display means 102, processes information from the measuring means 101, and transmits this information to the display means 102.

The numeral 107 denotes a database in the medical treatment planning means. In this database 107, information from the above measuring means 101 and information on the patient and affected area obtained beforehand are stored. The numeral 108 denotes a transmission path of instructions and information in the medical treatment planning means. This medical treatment planning means 104 is connected also to a network outside the medical treatment apparatus proper. The numeral 109 denotes the above external network group, the numeral 110 routers between networks, the numeral 111 a computer for medical treatment planning located in a remote place, and the numeral 112 a database connected to the computer 111. Further, the numeral 113 indicates instructions sent from the medical treatment planning means 104 to the network group 109 and instructions requiring the acquisition of information, and the numeral 114 denotes answers from the computer located in a remote place.

In later descriptions, "calculated objects" may be what contains in itself both or either of what is processed and a description of procedure for processing it. In other words, this term indicates an object that is composed of either or both of data in a general sense of the word and a program (code).

Further, the numeral 117 denotes a transmission path of instructions and information between the medical treatment plan controlling portion 105 and the measuring means, the numeral 118 a transmission path of data between the measuring means and the display means, and the numeral 119 a transmission path of instructions and information between the display means and the medical treatment plan controlling portion. The numeral 120 denotes a measuring action performed by the measuring means in order to obtain information on the condition of the patient and affected area, and in actuality, it indicates energy, such as an electromagnetic wave, light, ultrasound and radioactivity, etc. emitted, conducted or radiated from the measuring means 101. The numeral 121 denotes a reaction which is caused to occur from the affected area or patient by the above measuring action, and in actuality, it indicates a signal in the form of heat, light, sound, current, electromagnetic wave, etc. The numeral 122 denotes a medical treatment action to the patient and effected area by the medical treatment means 103, the numeral 123 a reaction from the affected area and patient which is generated by the above medical treatment action 122, and the numeral 124 a transmission path of instructions and information between the display means 102 and the medical treatment means 103.

The numeral 125 denotes a transmission path of instructions and calculated object between the medical treatment means 103 and the medical treatment plan controlling portion 105, and the numeral 126 indicates a operation-input action for the operation of the treatment means by a doctor who performs the surgical operation and uses the medical treatment apparatus. The numeral 127 denotes information which is obtained by processing the reaction 123 of the patient and affected area in a form easily understandable to the doctor who performs the surgical operation, which is expressed in the form of various kinds of energy, such as reaction force and heat, and which is given to the doctor via a operation-input portion (which will be described later). The numeral 128 denotes instructions given through the use of an interface of various kinds of modes (which will be described later) in order to operate the display means. The numeral 129 denotes information on the patient and affected area obtained by the measuring means 101 and information on a medical treatment plan from the medical treatment planning means 104, and the doctor who performs the surgical operation and uses the apparatus carries out the medical treatment while referring to the above information. This information includes also information which presents opinions, etc. of doctors present outside the treatment room in an integral manner and is expressed in the form of image, sound, heat, etc. The numeral 130 denotes the doctor who performs the surgical operation and uses the apparatus, and the numeral 131 denotes the patient on whom the operation is performed.

The doctor 130 who performs the surgical operation and uses the apparatus carries out necessary medical treatment for the affected area via the medical treatment means 103 by performing the operation-input action 126 while referring to the information 129 presented by the display means 102 and the information 127 presented by the medical treatment means 103.

The measuring means 101 has a plurality of measuring methods and measures the condition of the affected area and patient according to the timing given by the medical treatment plan controlling portion 105 through the transmission path during the medical treatment. Information obtained by measurement is sent to the medical treatment plan controlling portion 105 through the transmission path 117 and, at the same time, the same information is sent to the display means 102 through the transmission path 118. Further, the user 130 performs measurement also when he or she has issued instructions for obtaining information on the affected area and patient, which are a kind of command 128, through the transmission path 118 by way of an input means to the display means 102, and obtained information is sent to the medical treatment plan controlling portion 105 and display means 102 in the same manner as with the above information.

The measuring means 101 conducts or radiates energy, such as an electromagnetic wave, light, ultrasound and radioactivity, in order to obtain information on the condition of the patient and affected area. This results in the detection of signals 121 of heat, light, sound, current, electromagnetic wave, etc. which are secondarily induced in the affected area or caused to transmit, reflect or dissipate while being attenuated by the given energy 120 or which are actively given forth from the patient or affected area. The measuring means 101 obtains aimed information by appropriately processing these signals. Details will be described later.

The display means 102 presents the information 129 mainly composed of images, sounds and voices to the user. By way of the interface 128, which is input means, the user operates and controls the contents, kinds, appearances, etc. of the information presented by the display means. The display means 102 presents information on the patient and affected area obtained by the measuring means 101. At the same time, the display means presents medical treatment plan information which is sequentially modified and updated by the medical treatment planning means 104 and sent through the transmission path 119.

This medical treatment plan information contains information on the process of medical treatment, i.e., the procedure for medical treatment and operation of medical treatment. This information contains what specifies the behavior of the medical treatment means 103, for example, an updated approach orientation and amount of movement of the treatment means, an updated contact-prohibitive region, etc. Furthermore, this information contains the order of use of a plurality of surgical apparatus, such as the manipulator of the medical treatment means 103 and a surgical laser knife, and a plurality of measuring instruments of the measuring means 102. In addition, in this example, information on the coordinates and amounts of movement of the manipulator from the medical treatment means 102 is also made visual and audible and is displayed by the measuring means 102. Therefore, the medical treatment plan information also contains the order of displaying information obtained from the measuring means 101 in the above medical treatment means 103. Details will be described later.

The treatment means 103 receives and interprets the operation which is input by the user in order to perform a medical treatment action, and performs the medical treatment action to the affected area-according to the interpretation. At the same time, the medical treatment means 103 detects the reaction 123 caused by this action and gives the information 127 which is obtained by converting and processing the reaction 123 into a size, quantity and kind easily understandable to the user, and which is expressed in the form of various kinds of energy, such as reaction force, heat and vibration, via a manipulation input portion (which will be described later).

Also, the treatment means 103 sends information obtained by translating the condition of various kinds of internal mechanisms, coordinates of surgical instruments or the reaction 123 in the form of image, sound and voice to the display means 102 via the transmission path 124. Further, by way of the transmission path 125, the medical treatment means 103 obtains information for specifying the behavior within the internal mechanisms from the medical treatment plan controlling portion 105. This information is, for example, a new approach orientation and amount of movement, an updated contact-prohibitive region, etc. as mentioned above. Details will be described later.

The medical treatment planning means 104 comprises several elements. They are, for example, the medical treatment plan controlling portion 105, the medical treatment planning engine 106, the database 107, and the transmission path 108 of the calculated objects between the network group, which will be described later.

The medical treatment plan controlling portion 105 regulates the operation of the medical treatment planning means 104 and performs an information interchange with other means. First by way of the transmission path 117, the medical treatment plan controlling portion 105 makes a request for the acquisition of information to the measuring means 101 at a predetermined timing and obtains information of images, etc. as the information on the condition of the patient and affected area obtained by the measuring means 101 to meet the request. The medical treatment plan controlling portion 105 stores this information in the database 107 through the transmission path 108.

In the database 107 have so far been stored information from the above measuring means 101 and medical treatment means 103 and information obtained beforehand on the patient and affected area, for example, the position and shape of the affected area, images showing them, what is called vital signs, such as the pulse rate, blood pressure, temperature, etc. of the patient and affected area, etc., and the medical treatment plan computing means 106 makes calculations for modifying and updating a medical treatment plan by using the information stored here. When during the calculations it becomes necessary to refer to the past information of the patient, the medical treatment plan computing means 106 makes the request 113 for sending this information to the network group through the transmission path 108. When the necessary information 114 is obtained at the request, the medical treatment plan computing means 106 adds this information to the information presently held in the database 107, and makes calculations by processing this information. Calculation results are sent to the treatment plan controlling portion 105 through the transmission path 108, and the medical treatment plan controlling portion 105 receives the calculation results and sends modified and updated medical treatment plan information to the display means 102 and medical treatment means 103 through the transmission path 119 and transmission path 125.

After receiving the request for sending information 113, the network group 113 operates as follows.

The network which has received the request for sending information searches for a host having the required information and sends the information when this host is found. When this host is not found, a router which connects this network to other networks relays the above request to an upper-level network. In this manner hosts are searched for one after another to find a host having the information, and when the host in question has been finally found, the necessary information 114 is sent through a path reverse to the present path. Incidentally, when the desired host is not found even when the request has been relayed up to a certain level, the relaying is discontinued and the router which has discontinued the relaying sends back notification to that effect through a path, reverse to the present path.

Figure 2:
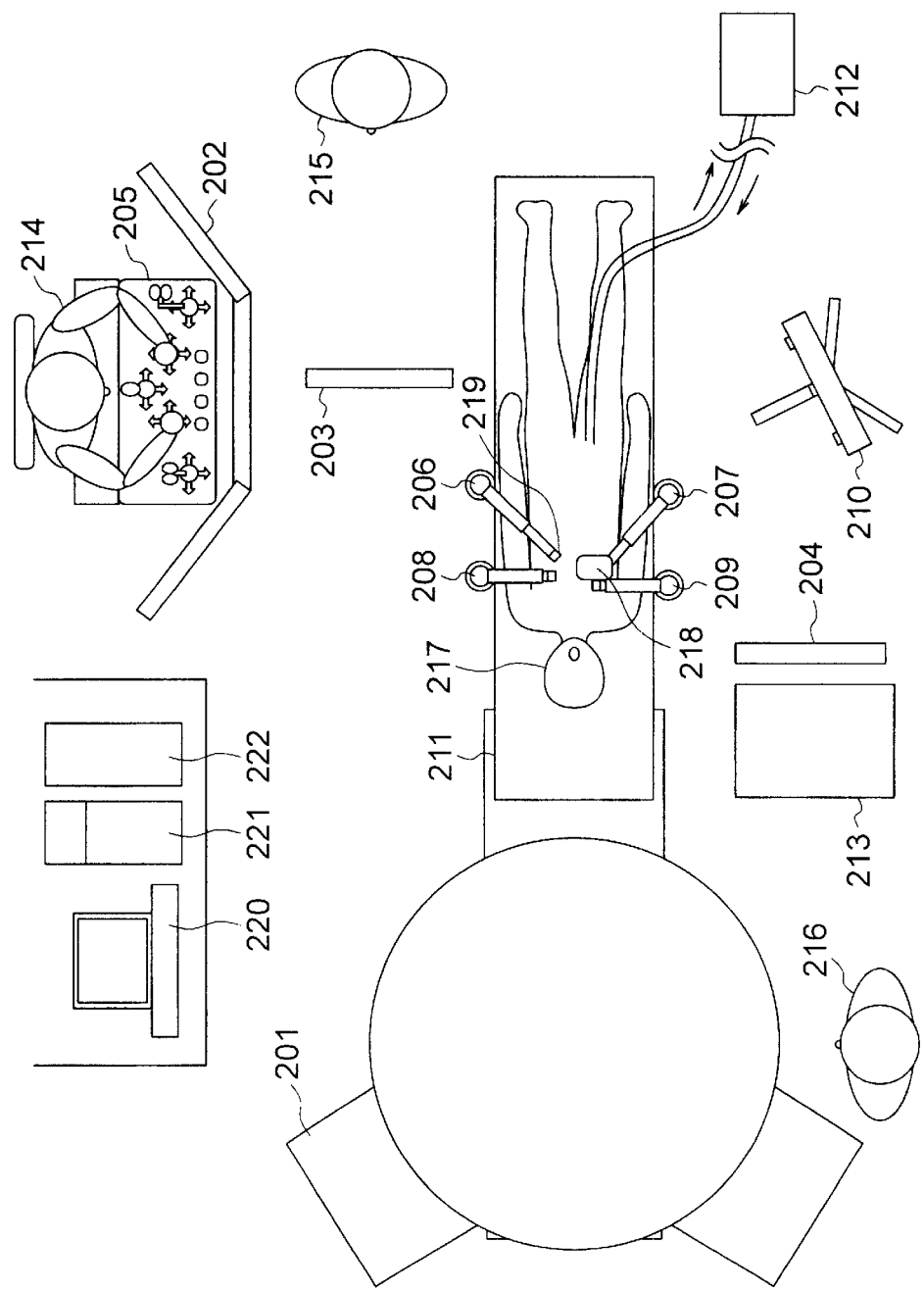
FIG. 2 is a schematic view of an embodiment of the invention.

FIG. 2 is a schematic drawing of an embodiment of the invention. In the drawing, the numeral 201 denotes an open MRI and the numeral 202 denotes a flat-panel display that provides display means for a user. This display 202 is composed of three individual displays 202, 203 and 204, each of which can display information set for each user of the apparatus in this embodiment. The numeral 203 denotes a flat-panel display for an assistant, the numeral 204 a flat-panel display for an anesthetist, the numeral 205 an operation-input console, the numeral 206 a holding device of ultrasonic scanner probe, the numeral 207 a holding device of manipulator for fine manipulation, the numerals 208 and 209 holding devices for lifting the affected area and opening the chest, the numeral 210 a three-dimensional position-orientation-measuring device, the numeral 211 a slide-type bed, the numeral 212 an auxiliary extracorporeal oxygenerator to be used in an emergency, the numeral 213 a place where chemicals and instruments to be used by the anesthetist are placed, the numeral 214 a user (a doctor ho performs a surgical operation), the numeral 215 an assistant, the numeral 216 an anesthetist, the numeral 217 a patient, the numeral 218 a manipulator for fine manipulation, the numeral 219 an ultrasonic scanner probe, the numeral 220 a computer for medical treatment plan control, the numeral 221 a computer for medical treatment plan computing, and the numeral 222 a database machine for medical treatment plans.

The open MRI 201 and ultrasonic scanner probe 219 are included in the above measuring means 101. The displays 202, 203 and 204 are included in the display means 102. The operation-input console 205, holding device of ultrasonic scanner probe 206, holding device of manipulator for fine manipulation 207, holding devices for lifting the affected area and opening the chest 208 and 209, three-dimensional position/orientation-measuring device 210, slide-type bed 211, and manipulator for fine manipulation 218 are included in the medical treatment means 103. The auxiliary extracorporeal oxygenerator 212 is provided so that it can be used when the circulation condition of the patient becomes worse. In the place where chemicals and instruments are placed 213, chemicals which the anesthetist give to the patient while observing the condition of the patient and instruments to be used on that occasion are put. While receiving information in the form of image, etc., which information is presented by the display 202, and information based on the sense of force and the sense of touch, such as a reaction force, vibration, heat, etc., which information is generated and transmitted by an operation-input lever of the console 205, the user 214 adjusts the positions and orientations of each of the holding devices 206 to 209 and the position of the bed 211, as necessary gives instructions requiring the acquisition of image information obtained by the open MRI 201 and the ultrasonic scanner probe 219 and coordinate values of position and orientation at object points (the affected area, leading end of the manipulator 218, etc.) in the standard coordinates obtained by the three-dimensional position/orientation-measuring device 210, and performs medical treatment by remote-controlling the manipulator for fine manipulation 218 via the operation-input lever. The computers 220 to 222 are a group of computers which constitute the medical treatment planning means. The computer 220 serves the medical treatment plan controlling portion 105, the computer 221 serves the medical treatment plan engine 106, and the computer serves the database 107.

These computers are installed either inside or outside the operating room and are connected to each other and to other corresponding structural components by cable or radio transmission paths. Incidentally, these transmission paths, network group, etc., are not shown in the figure to prevent the drawing from being difficult to see.

Figure 3:
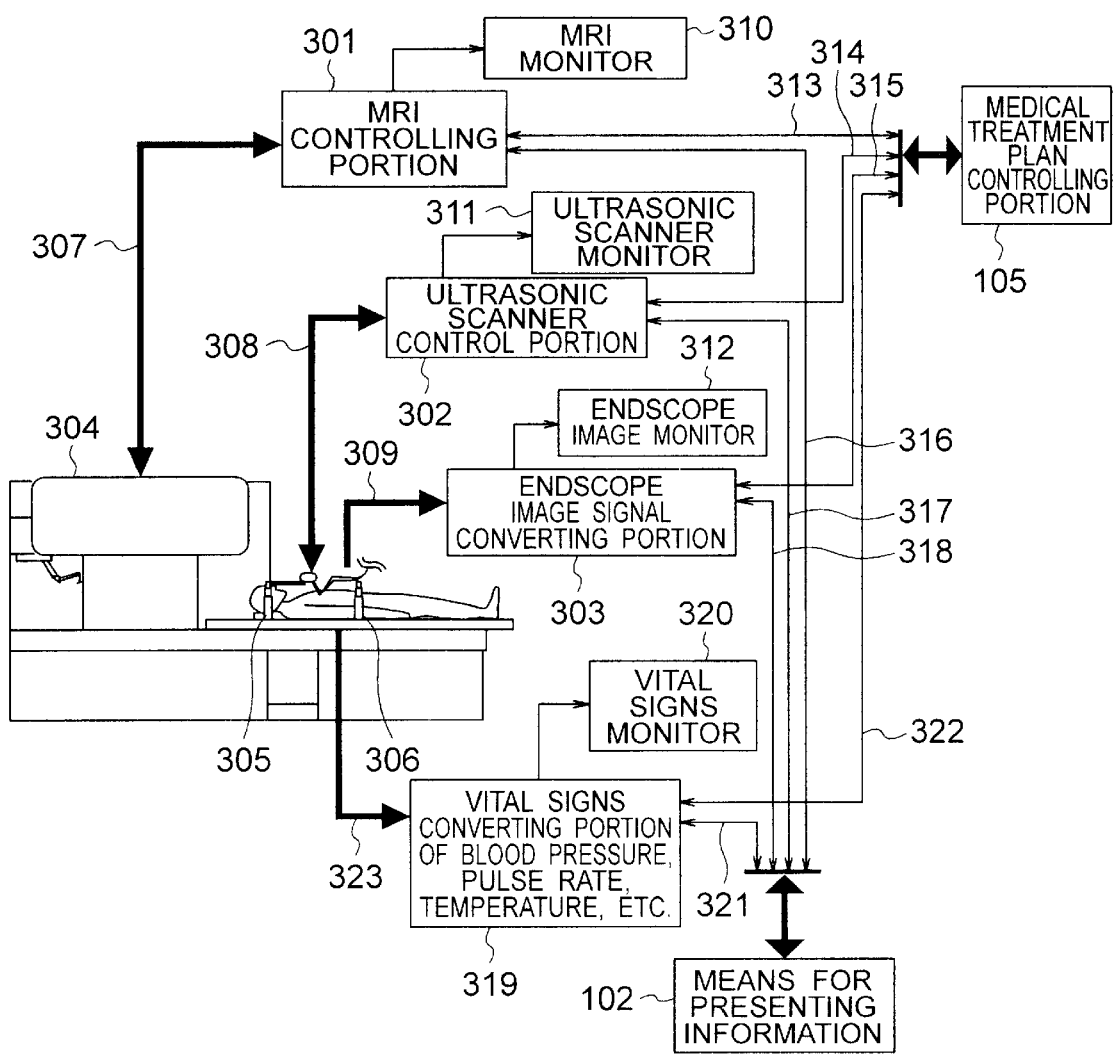
FIG. 3 is a schematic view of an internal configuration of measuring means 101.

FIG. 3 shows an internal configuration of the measuring means 101. In the figure, the numeral 301 denotes an MRI control portion, the numeral 302 an ultrasonic scanner control portion, the numeral 303 an endscopic image signal converting portion, the numeral 319 a signal converting portion of vital signs, such as blood pressure, pulse rate and temperature, the numeral 304 an pen MRI, the numeral 305 a holding device of manipulator or fine manipulation, the numeral 306 a holding device of ultrasonic scanner probe, the numeral 307 a transmission path of instructions and signals between the MRI proper and the MRI control portion, the numeral 308 a transmission path of instructions and signals between the ultrasonic scanner proper and the ultrasonic scanner control portion, the numeral 309 a transmission path of endscopic images, the numeral 323 a transmission path of vital sign signals, the numeral 310 an MRI image monitor, the numeral 311 an ultrasonic scanner image monitor, the numeral 312 an endscopic image monitor, the numeral 320 a vital sign monitor, the numeral 313 a transmission path of instructions and image information between the MRI control portion and the medical treatment plan controlling portion 105, the numeral 314 a transmission path of instructions and image information between the ultrasonic scanner control portion and the medical treatment plan controlling portion 105, the numeral 315 a transmission path of instructions and image information between the endscopic image signal converting portion and the medical treatment plan controlling portion 105, the numeral 321 a transmission path of instructions and image information between the vital sign signal converting portion and the medical treatment plan controlling portion 105, the numeral 316 a transmission path of instructions and image information between the MRI control portion and the display means 102, the numeral 317 a transmission path of instructions and image information between the ultrasonic scanner control portion and the display means 102, the numeral 318 a transmission path of instructions and image information between the endscopic image signal converting portion and the display means 102, and the numeral 322 a transmission path of instructions and image information between the vital signs converting portion and the display means 102. Incidentally, detection means of blood pressure, pulse rate, temperature, etc., are not shown in the figure.

The MRI control portion 301, ultrasonic scanner control portion 302 and endscopic image signal converting portion 303 change images and operating condition in accordance with instructions from the medical treatment plan controlling portion 105 or instructions from the user transmitted via the display means 102. Instructions from the medical treatment plan controlling portion 105 are periodically sent and images are updated at intervals of a fixed period of time. Instructions from the user are asynchronously sent and images are updated also at the occasion.

In any case, however, endscopic images are constantly taken at a video rate. Vital sign signals of blood pressure, pulse rate, temperature, etc. are constantly monitored. Taken images and image information are sent to the medical treatment plan controlling portion 105 through the transmission paths 313 to 315 and 321 and to the display means 102 through the transmission paths 316 to 318 and 322. The information sent on that occasion may be sent and received in the form of analog signal such as a video signal or in the form of digital data.

Figure 21:
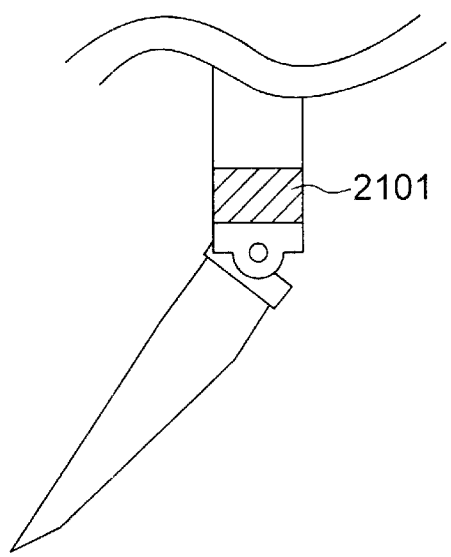
FIG. 21 is an explanatory view illustrating a method of detecting the leading end of a manipulator by MRI.

The measuring means 101 is used also to detect the position of the leading end of the manipulator for fine manipulation (which will be described later). For this purpose, as shown in FIG. 21, a substance 2101 whose image is taken in a high signal, such as an RF coil or a fat, is placed before the bent portion of the leading end of manipulator. By taking an image of this substance by MRI and detecting its position from the image, it is possible to navigate the manipulator. Furthermore, because the position of the leading end of the manipulator can be detected in the MRI image, the alignment with the operation coordinates of the manipulator can be easily performed.

Figure 4:
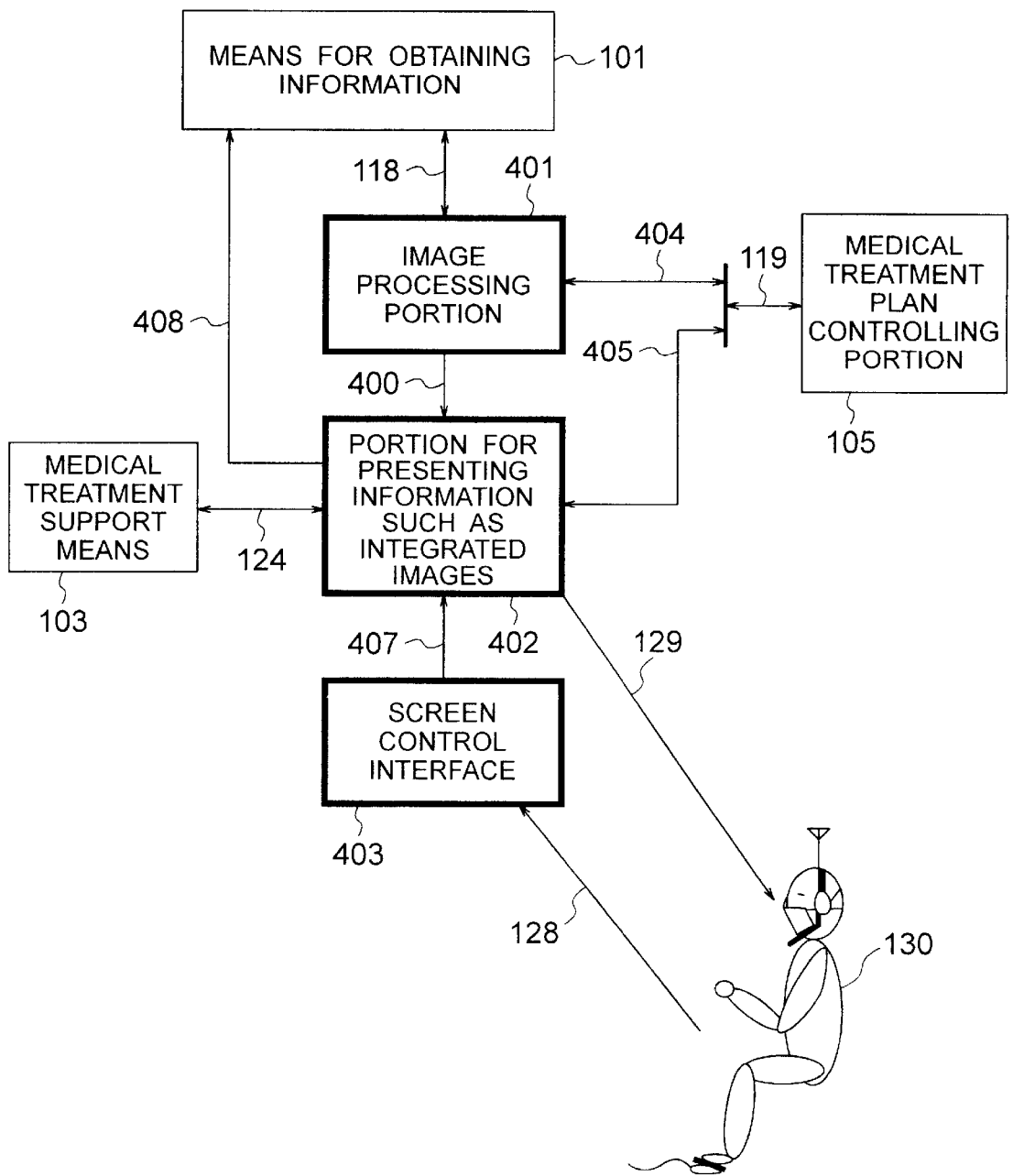
FIG. 4 is a schematic view of an internal configuration of display means 102.

The display means 102 is described below. FIG. 4 shows an internal configuration of the display means. In the figure, the numeral 401 denotes an image processing portion, the numeral 402 a portion for presenting information such as integrated images, the numeral 403 a screen control interface, the numeral 404 a transmission path of instructions between the image processing portion 401 and the medical treatment plan controlling portion 105 and of image information obtained by the measuring means 101, the numeral 405 a transmission path of instructions and medical treatment plan image information between a portion presenting information such as images 402 and the medical treatment plan controlling portion 105, the numeral 406 a transmission path of processed image information, the numeral 407 a transmission path of the user's screen control instructions and information acquisition instructions to the measuring means input via the interface 403, and the numeral 408 a transmission path of information acquisition instructions to the measuring means.

The image processing portion 401 processes image information sent from the measuring means 101. When the information is analog signals, it is first converted into digital information. This operation can be omitted when digital information is sent from the beginning. Next, for performing plane or three-dimensional drawing on the basis of image information from each converted modality, computing operations, such as noise removal, interpolation calculation, adjustment of brightness and color tone and volume rendering, are performed. Processed image information is sent to the information presenting portion 402 through the transmission path 406 and to the medical treatment plan controlling portion 105 through the transmission path 404. The information presenting portion 402 integrates image information from each modality, medical treatment plan images, user guidance image information, and coordinate information and operating information of the manipulator from the medical treatment means, and presents the integrated information in the form prescribed by the user via the screen control interface 403. On that occasion, user guidance information and information on the operation of the manipulator are presented in combined use of voices with images. For example, in a case where a reference trajectory is indicated as the navigation information for the manipulator, the above sound includes an alarm sound given forth when the navigator performed a motion deviating from the trajectory and an alarm sound given forth when the manipulator is approaching a region in tissue which is defined in a medical treatment plan as a contact-prohibitive region. Details of the screen control interface will be described later.

Figure 5:
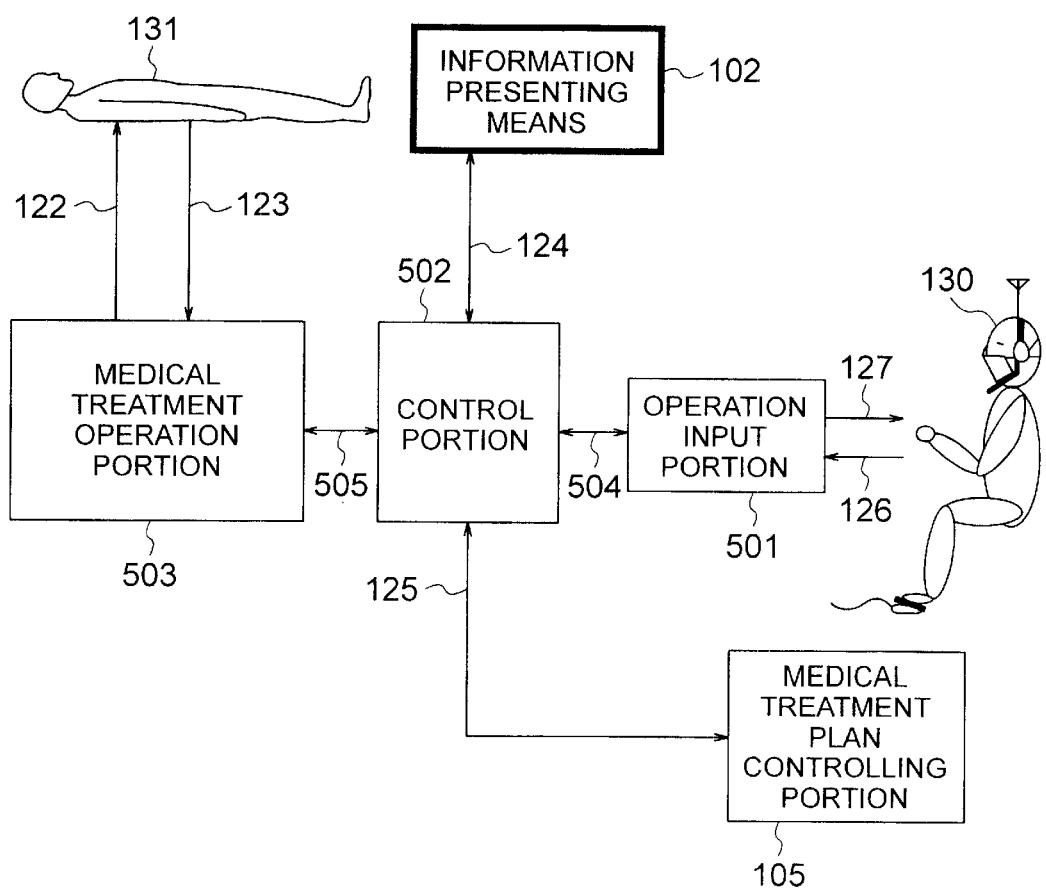
FIG. 5 is a schematic view of an internal configuration of medical treatment means 103.

FIG. 5 shows an internal configuration of the medical treatment means. In the figure, the numeral 501 denotes an operation-input portion, the numeral 502 a control portion, the numeral 503 a medical treatment operation portion, the numeral 504 a transmission path for sending and receiving instructions and data between the operation-input portion 501 and the control portion 502, and the numeral 505 a transmission path for sending and receiving instructions and data between the control portion 502 and the medical treatment operation portion 503.

The operation-input portion 501 detects various bodily and physiological changes which are uniquely and optionally produced according to the intention of the user and sends this information to the control portion 502 through the transmission path 504. Bodily and physiological changes are, for example, expansion and contraction of muscles in each part of the body, movement of the eyeballs, voice, electroencephalogram or magnetoencephalographic distribution, distribution of active portions in the brain, etc. Examples of method of detecting these bodily and physiological changes are as follows. For instance, the expansion and contraction of muscles may be detected by mechanical means, such as the movement of an operation lever, a foot switch, etc., or electrical means, such as muscle current detection, or chemical means, such as the detection of the concentration of a substance generated by the movement of muscles. The movement of the eyeballs may be detected by optical means such as an eye tracker, and voices may be detected by electro-acoustic means such as a microphone. It is possible to detect electroencephalogram by means of a electroencephalographer, magnetoencephalographic distribution by means of a magnetoencephalographer using a squid, and the distribution of active portions in the brain by means of a functional MRI.

After receiving information detected in the operation-input portion 501, the control portion 502 interprets the kind and value of the information and gives instructions about details of operation addressed to the subjects of operation, which have been related to the information beforehand, to the medical treatment operation portion. Subjects of operation refer to the holding devices 206 to 209, manipulator for fine manipulation 218, bed 211, various surgical instruments and stabilizers, etc. The details of instructions given on that occasion are simultaneously sent to the display means 102 via the transmission path 124. The display means 102 performs the imaging of instructions and presents images thus produced in combination with medical treatment plan images, actual kinematical information (which will be described later), etc.

At these instructions the medical treatment operation portion 503 performs a medical treatment operation by moving the assigned subjects of operation in accordance with values. Subjects of operation which directly receive reactions from an object of medical treatment during a medical treatment operation detects the reactions and returns this information to the control portion 502. The control portion 520 interprets this information and performs computing such as noise processing and scaling. When it is considered appropriate to communicate information on detected reactions by the sense of touch and the sense of force, such information is sent to the operation-input portion, where the information is presented to the user in the form of movement of an operation lever, etc. Information of this kind includes information on the sense of proximity during the approach of the manipulator, information on a reaction force during contact or holding with a surgical instrument, information on the temperature of the affected area detected by the leading end of the manipulator, etc.

On the other hand, when it is considered appropriate to present information in the form of image, sound and voice, such information is sent to the display means 102 via the transmission path 124. The above information is processed beforehand so that it can be presented also in the form of image, sound and voice according to an actual condition. At the same time, to the transmission path 124 is sent the kinematical information of each subject of operation (for example, the manipulator for fine manipulation, which will be described later) included in the medical treatment operation portion 124. All the above information is presented by the display means 102 in the form of image, sound and voice.

Examples related to the above descriptions are shown below.

As an example of operation-input portion there is a type such as the console 205. For example, the user intends to change the position and posture of the manipulator for fine manipulation, which is one of the medical treatment means, and moves his or her muscles in each part of the body, mainly, the arms, in order to bring down an operation lever. The operation lever is provided in each joint with sensors for detecting the displacement of the joint, such as a potentiometer, encoder, and tachometer.

The fact that the operation lever was brought down and the displacement of each joint are communicated to the control portion 502. In the control portion 502, bringing down the operation lever is beforehand related to bending the joints of the manipulator for fine manipulation. The control portion 502 gives instructions to the manipulator for fine manipulation to appropriately move each joint. Instructions may sometimes be given at a level of joint space or may sometimes be given at a level of operation coordinates when the mechanism of the operation lever is different from that of the manipulator for fine manipulation. In order to prevent unintended involuntary movements of the hands in bringing down the operation lever, the filtering of instruction values is performed or scheduling of instruction values (generally, an isotropic scheduling), in which the size of the operation lever and manipulator and the fineness of work are considered, is performed. These instruction values are sent to the display means 102, where these values are converted into images and presented.

The manipulator for fine manipulation operates by the designation of the subject of operation by the control portion 502 and at operation instructions from the control portion 502. During the operation, proximity information is detected by a sensor in the case of a contacted condition and a reaction force is detected by a sensor in the case of a contacting/holding condition. In both conditions, the temperature (or quantity of infrared radiation emissions) of an object point is detected. Detected sensor information is sent to the control portion 502. The control portion 502 interprets this information and performs the computations of the information, such as noise processing and scaling. Information on reaction force and temperature among the detected reactions is sent to the operation-input portion 501. The operation-input portion 501 presents the information to the user by driving the operation lever in the case of a reaction force and by warming/cooling the lever in the case of temperature.

The above sensor information is simultaneously presented in the form of image, sound and voice at the request of the user. In other words, this information is sent to the display means 102 via the transmission path 124, where the information is presented in the form of graph, CG, etc., or by reading-out in synthetic voice, or by means of a musical interval, type of sound, sound volume, tone, harmony, etc.

At the same time on that occasion, the kinematical information of the manipulator is sent to the transmission path 124. All such information is presented by the display means in the form of image, sound and voice. In this case, on the basis of the displacements of each joint and their n-order differentiation, CGs of the manipulator are generated and the information on reactions during contact is presented, in the case of an image, by a change in the shape of a drawn figure, the speed of the change, kind, brightness, chroma, etc. of a color, etc. and presented, in the case of a sound, by the reading-out in a synthetic voice, or by means of a musical interval, type of sound, sound volume, tone, harmony, etc.

Furthermore, on that occasion, in the medical treatment planning means 104, the medical treatment plan control portion 105 gives instructions to the medical treatment plan engine 106 to calculate control information which specifies the operation of the medical treatment means, such as the manipulator, for realizing a procedure for medical treatment and each procedure. On the basis of a plurality of kinds of image information and vital sign information which have until this point in time been obtained and stored in the database 107 by the measuring means 101 at the timing sequentially specified by the medical treatment plan control portion during the medical treatment, the medical treatment plan engine 106 performs the detection of changes in the position, orientation and shape of internal organs including the affected area in question and detects whether the condition of the patient changes or not, further calculates and derives from the above information the speed, direction, allowed operating range, arrival-prohibitive region, etc. of the manipulator, and also information on the output, irradiation time, etc. of a laser knife, which is one of the surgical instruments. The medical treatment plan control portion communicates this information to the control portion 502 in the medical treatment means 103, and the control portion 502 uses this information as control information of the manipulator and surgical instruments such as the laser knife.

Figure 6:
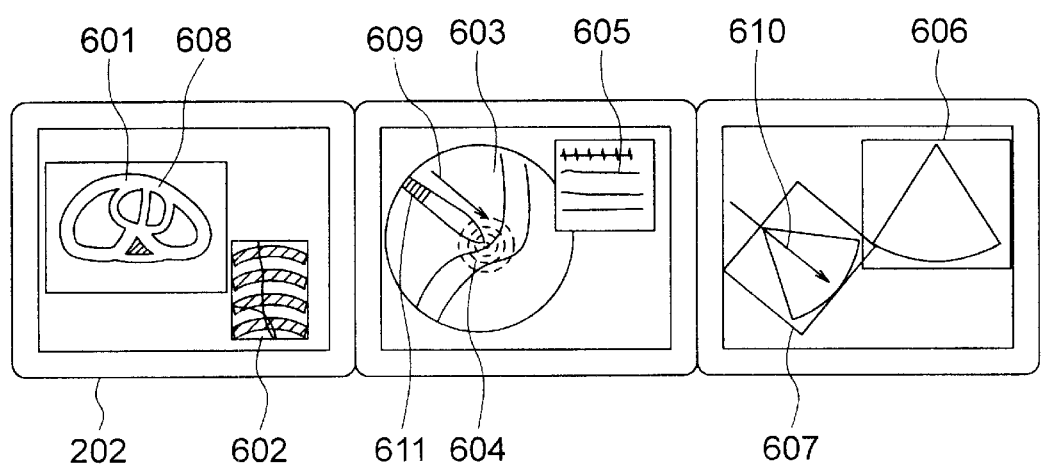
FIG. 6 is an illustration of an example of information presented by display means.

FIG. 6 shows an example of information presented by the display means. In the figure, the numeral 601 denotes an MRI image, the numeral 602 an MRA image, the numeral 603 an endscopic image, the numeral 604 proximity information, the numeral 605 vital sign information, the numeral 606 an ultrasonic scanner image of the body surface, the numeral 607 an image from an ultrasonic scanner installed at the distal end of the manipulator, the numerals 608, 609 and 610 each medical treatment plan information, and the numeral 611 reaction force information.

The MRI image 601 is periodically taken and sequentially updated. Although usually this MRI image is presented as a shape image, before the seaming of an incision a function image is taken and presented in order to observe the recovery condition of the tissue, etc. On the MRI image 601 is superimposed the medical treatment plan information 608. In the figure, the start point of an arrow indicates the present position of the distal end of the manipulator and the arrow itself indicates an optimum travel direction. Although mainly an image before the surgical operation is shown as the MRA image, images are taken also before the seaming of the incision thereby to observe the patency condition of blood vessels, etc.

The endscopic image 603 is sequentially presented. On the endscopic image 603 are superimposed the proximity sense information 604, which is manipulator sensor information, the reaction force information 611, etc. Further, the medical treatment plan information 609 is presented along with them. In the medical treatment plan information 609, an arrow indicates an optimum travel direction of the manipulator. While referring to this information, the user operates the manipulator considering the next operating direction, movement distance, etc. As the vital signs information 605, changes in blood pressure, pulse rate, temperature, etc. are sequentially and continuously displayed.

The numeral 606 denotes an ultrasonic scanner image of the body surface. The numeral 607 denotes an image from an ultrasonic scanner installed at the distal end of the manipulator. On this image 607 is superimposed an optimum travel direction of the distal end of the manipulator as the medical treatment plan information.

Incidentally, the manipulator provided with an ultrasonic scanner at the leading end thereof may be the same manipulator that performs a medical treatment operation or it may be another manipulator. This will be described later.

The nature of each of the above information is described here. The MRI image 601 shows a general structure including the affected area. The ultrasonic scanner images 606 and 607 show a local structure of an affected organ and portion on which medical treatment it to be performed. In particular, these images can display the portion under the surface of the affected organ in question, i.e., the structure which cannot be seen with the naked eye or by optical means. In contrast to this, the endscopic image 603 is a magnified view of a portion which requires an especially detailed observation at a certain step during the medical treatment.

Incidentally, the medical treatment plan information 608, 609 and 610 provides very simple examples, in which by incorporating information on changes in condition, such as deformation and movement, which occur during the operation of a tissue in the surgical operation, the problem of collision avoidance to a vital tissue, etc. is solved again one after another each time image information is updated and results of the solution are shown.

Besides, as medical treatment plan information, a simulation image of deformation by one scheduled subsequent operation, corrected and modified points in a medical treatment scenario prepared on the basis of the information before the surgical operation alone, etc., are displayed.

Figure 7:
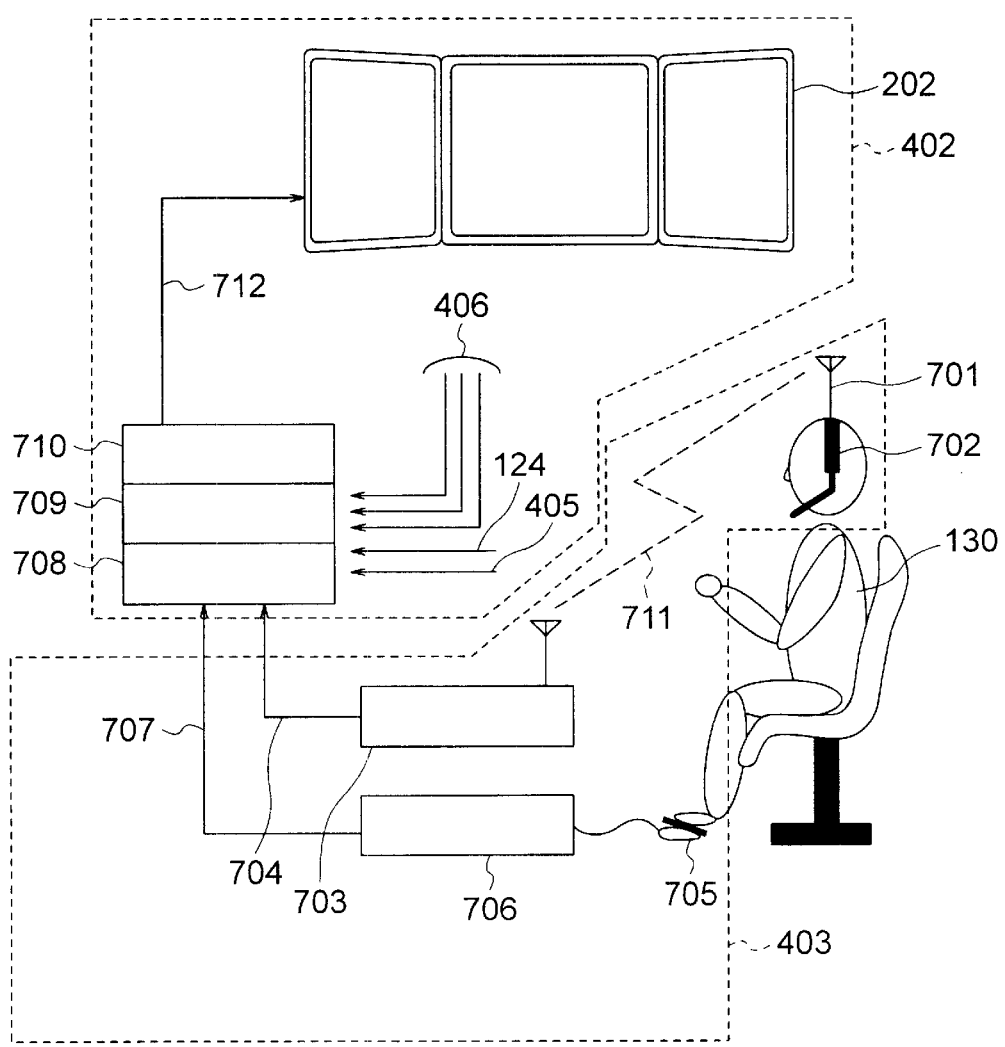
FIG. 7 is a schematic view of an internal configuration of a portion presenting information such as images 402 and a screen control interface 403.

Next, the internal configuration of the portion presenting information such as images 402 and the screen control interface 403 is explained by referring to FIG. 7. In the figure, the numeral 701 denotes an antenna which sends modulated electromagnetic waves, sonic waves, etc., to a receiving portion, the numeral 702 a microphone with a transmitter, the numeral 703 a receiver with a voice recognition portion, the numeral 704 a transmission path of results of recognition, the numeral 705 a footpedal, the numeral 706 a footpedal input detection portion, the numeral 707 a transmission path of results of footpedal input, the numeral 708 an information presenting and controlling portion, the numeral 709 an image superimposition-processing portion, the numeral 710 an image changeover-processing portion, the numeral 711 a transmission path of information including various kinds of instructions sent by the user to the display means or a transmission medium of electromagnetic waves, sonic waves, etc., and the numeral 712 a transmission path for sending information on images, sounds and voices, etc. generated by processing to the display.

The user 130 produces, according to his or her own intention, bodily and physiological changes which are unique and optional. These changes are detected by the microphone with a transmitter 702 and the footpedal 705, and information on changes detected by the microphone with a transmitter 702 is sent to the information presenting and controlling portion 708 via the transmission medium 711. The above detected information and the user's requirements are uniquely in agreement with each other, and the user can change the content and layout of information presentation by voices, movements of arms and legs, electroencephalographic wave, etc. Bodily and physiological changes are, for example, expansion and contraction of muscles in each part of the body, movement of the eyeballs, voice, electroencephalogram or magnetoencephalogram distribution, distribution of active portions in the brain, etc. In the figure are shown examples of detection of voice by the microphone 702 and detection of the expansion and contraction of the muscles of lower limbs by the footpedal.

Incidentally, as other examples of method of detecting bodily and physiological changes the following are conceivable. The expansion and contraction of muscles may be detected by mechanical means, such as the movement of an operation lever, a foot switch, etc., or electrical means, such as muscle current detection, or chemical means, such as the detection of the concentration of a substance generated by the movement of muscles. The movement of the eyeballs may be detected by optical means such as an eye tracker, and voices may be detected by electro-acoustic means such as a microphone. It is possible to detect electroencephalogram by means of a electroencephalographer, magnetoencephalogram distribution by means of a magnetoencephalographer using a squid, and the distribution of active portions in the brain by means of a functional MRI.

An example of use is described below. In order to change the content of presented image information, the user makes voice to the microphone 702 or treads the footpedal 705 by moving the lower limbs. The input from the microphone is modulated by the transmitter (not shown in the figure) and sent to the receiver with the voice recognition portion 703 through the transmission medium 711. The transmission medium in this case may be a conductor or what propagates through the air, for example, an electromagnetic wave, such as radio wave, light and infrared radiation, and an ultrasonic wave. Especially, an infrared wave and a supersonic wave are advantageous because they are free from interference with the magnetic field of MRI and can propagate through the use of a scattering by the wall and other equipment in the operating room.

The user's requirements which have been input are recognized and interpreted by the receiver with the voice recognition portion 703 and the footpedal 706, and sent to the information presenting and controlling portion 708 through the transmission paths 704 and 707.

To the information presenting and controlling portion 708 is sent the information of MRI images, ultrasonic scanner images and endscopic images, which are processed in the image processing portion 401, through the transmission path 406. Further, by way of the transmission path 124 are sent the kinematical information on the distal end position and orientation, coordinates, etc. related to the manipulator and other subjects of medical operation, which is sent from the control portion of the medical treatment means 103, and the environmental information at and near an object point detected by a proximity sensor, force sensor, temperature sensor, etc. In addition, the latest updated medical treatment plan information is sent via the transmission path 505. All the above information go may be transmitted in the form of analog signal or in the form of digital information.

Incidentally, the information on subjects of medical treatment operation sent via the transmission path 124 is subjected to a modality conversion in the information presenting and controlling portion 708 and is expressed in the form of image, sound and voice, etc. For example, this information is presented in the form of graph, CG, etc., or by reading-out in synthetic voice, or by means of a musical interval, type of sound, sound volume, tone, harmony, etc. In a case where the subject of medical treatment operation is the manipulator, on the basis of the displacements of each joint and their n-order differentiation, CGs of the manipulator in which the mechanism of the manipulator is three-dimensionally drawn are generated and the information on reactions during contact is presented, in the case of an image, by a change in the shape of a drawn figure, the speed of the change, kind, brightness, chroma, etc. of a color, etc. and presented, in the case of a sound, by the reading-out in a synthetic voice, or by means of a musical interval, type of sound, sound volume, tone, harmony, etc.

The information presenting and controlling portion 708 integrates and arranges each of the above information, determines the content and layout of presentation in accordance with the user's requirements, and sends instructions for realizing this to the image superimposition-processing portion 709 and the image changeover-processing portion 710. The image superimposition-processing portion 709 and the image changeover-processing portion 710 lays out images in accordance with the instructions from the information presenting and controlling portion 708 sends them along with the sound information generated in the information presenting and controlling portion 708 to thereby present them to the user.

Figure 8:
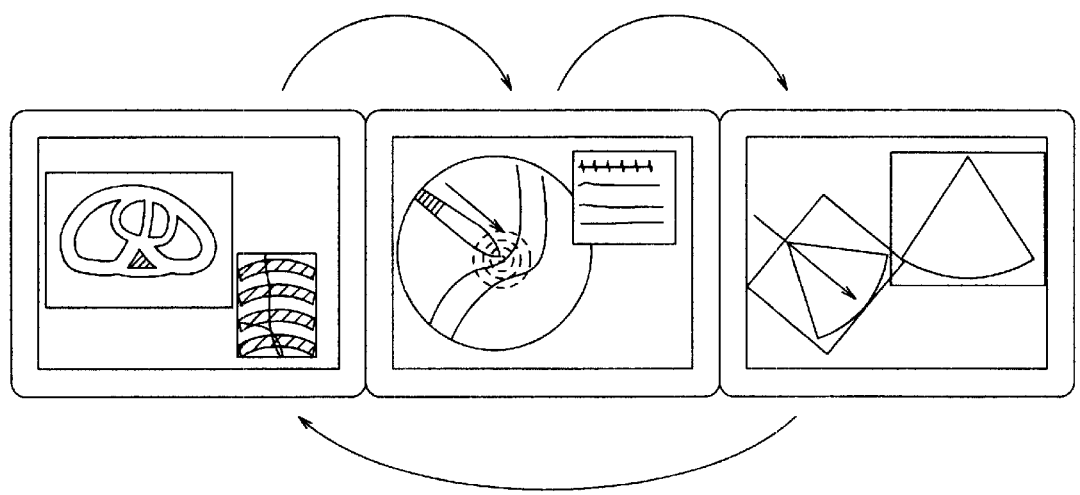
FIG. 8 is an explanatory view 1 of a change in layout.
Figure 9:
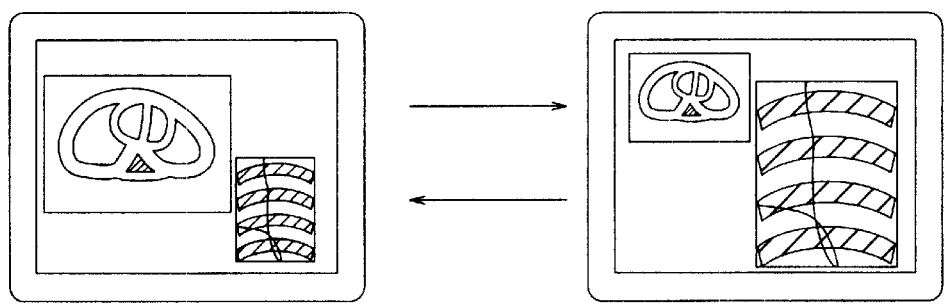
FIG. 9 is an explanatory view 2 of a change in layout.

Incidentally, a change of layout means, as shown in FIG. 8, replacement of the content of display on each display screen and display/nondisplay of medical treatment plan information and environmental information, or it means, as shown in FIG. 9, a selection of the content of display, a change of the size and arrangement of display, etc. on the same screen, etc.

Figure 10:
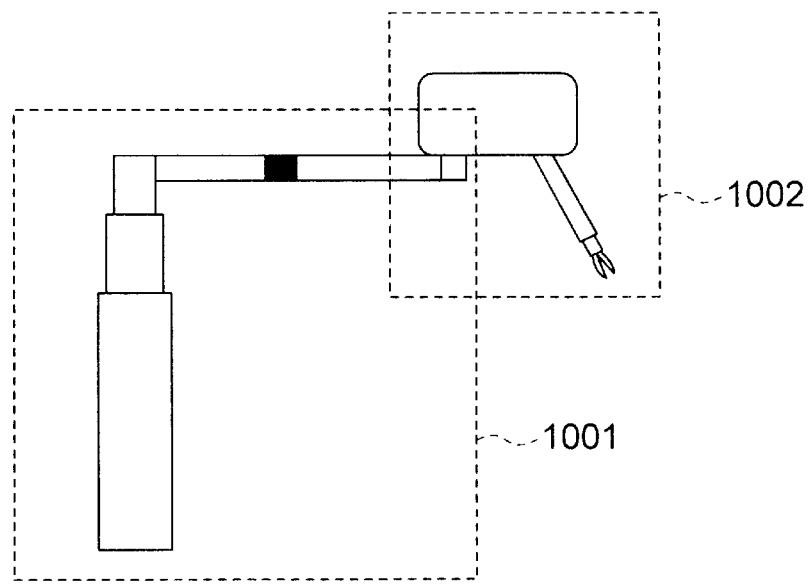
FIG. 10 is an illustration of an example of construction of a manipulator for fine manipulation and a holding device for holding the manipulator.

Next, an example of subject of medical treatment operation in the medical treatment operating portion 503 is explained with the aid of FIG. 10. FIG. 10 shows an example of construction of a manipulator for fine manipulation and a holding device for holding the manipulator. In the figure, the numeral 1001 indicates a holding device and the numeral 1002 a manipulator for fine manipulation.

The holding device 1001, which is a multiple-articulated link mechanism, can hold the manipulator for fine manipulation 1020 in an arbitrary position and orientation. As the material for the mechanical portion, nonmagnetic alloys or metals such as duralumin and titanium, or nonmetals such as engineering plastics and ceramics are used. As bearings those made from plastics or ceramics should be used. For the driving of each joint, an ultrasonic motor made of nonmagnetic substance alone and an actuator which uses fluid pressure, such as water pressure and pneumatic pressure, should be used. The holding device is assembled by the use of screws, bolts and nuts made of the above nonmagnetic metals (titanium, etc.) or adhesives. The above construction prevents the effect of a magnetic field of MRI. The same materials and principle of drive are used also for the manipulator for fine manipulation 1002.

Figure 11:
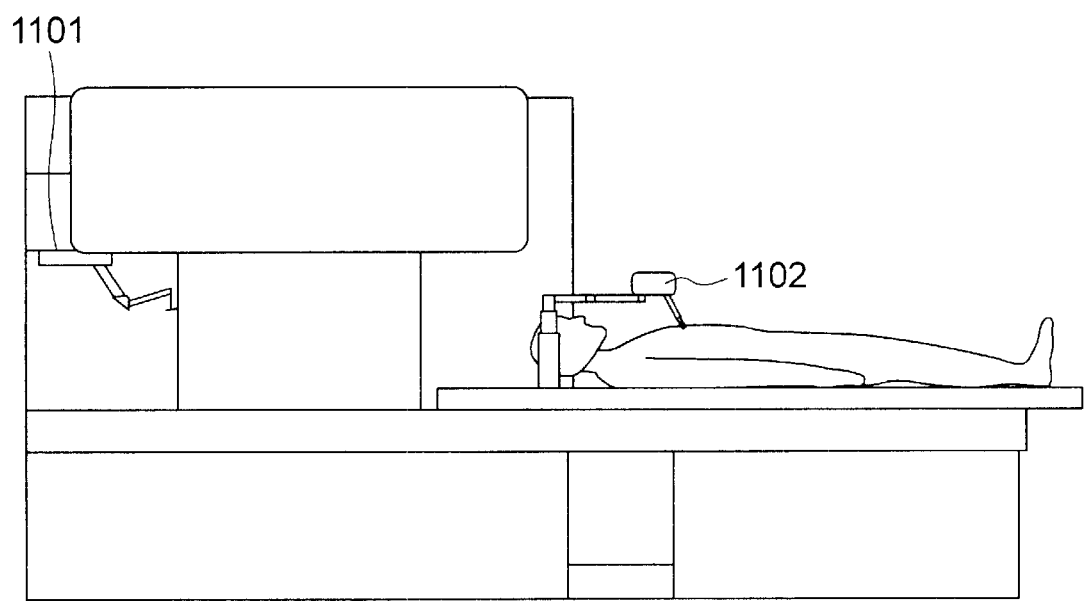
FIG. 11 is a schematic view of types of holding device installed in different places.

As shown in FIG. 11, the holding devices, manipulator, etc. held by them are either of a ceiling-suspension type or of a bedside type. The combined use of the two types enables congestion around the patient by the holding devices to be avoided when the patient enters the image-taking region of MRI.

Figures 13A, 13B, 13C, 13D, 13E:
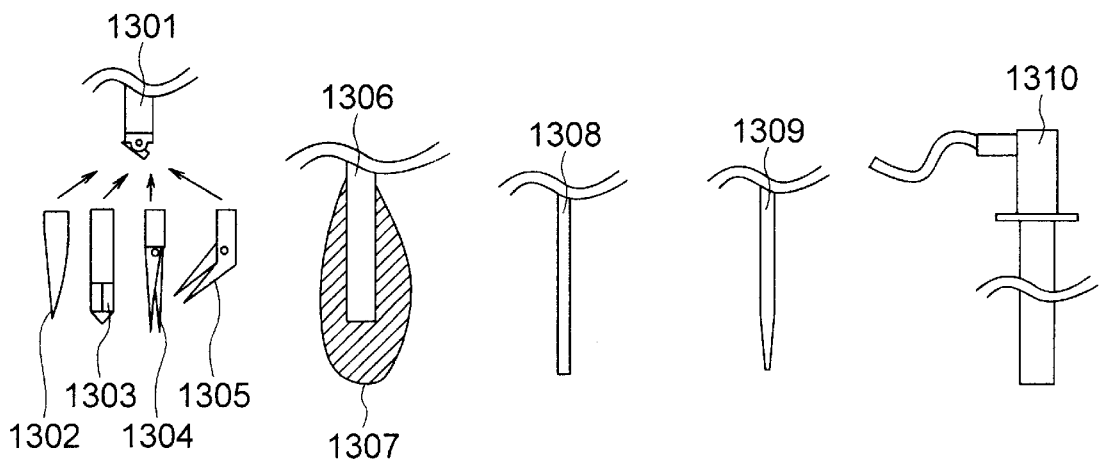
FIGS. 13A to 13F are schematic views illustrating examples of construction of a manipulator for fine manipulation.
Figure 13F:
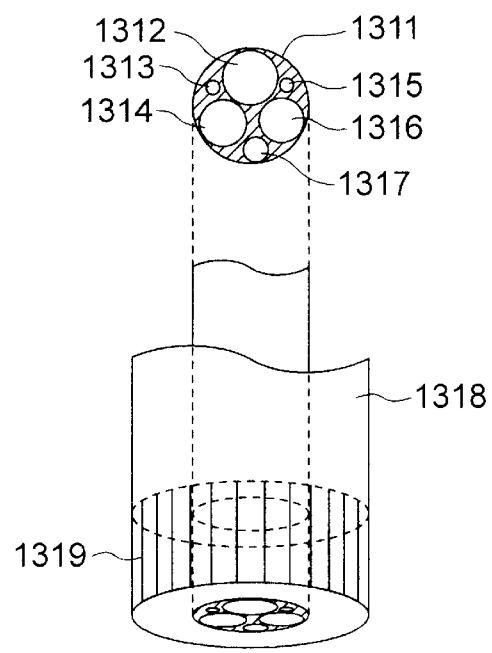

Next, examples of construction of manipulator for fine manipulation are described with the aid of FIGS. 13A to 13F. In FIG. 13A, the numeral 1301 denotes a distal end of the manipulator, the numeral 1302 a surgical knife, the numeral 1303 a knife, the numeral 1304 a pair of tweezers, and the numeral 1305 a pair of forceps. The surgical knife 1301 is a surgical instrument for incising an affected area, the knife 1303 for peeling a tissue, the pair of tweezers 1304 for holding a needle for seaming and anastomosis, and the pair of forceps 1305 for cutting open and cutting off the affected area. The surgical instruments 1302 to 1305 can be attached to and detached from the distal end 1301 of the manipulator.

Further, in FIG. 13B, the numeral 1306 denotes a water injection pipe and the numeral 1307 denotes a balloon made of a soft material; in FIG. 13C the numeral 1308 indicates a physiological saline solution feed pipe; in FIG. 13D the numeral 139 denotes a gas feed pipe for spouting carbon dioxide; and in FIG. 13E the numeral 1310 indicates an endscope. The physiological saline feed pipe 1308 is used to wash the affected area. The gas feed pipe 1309 is used to blow away blood when the affected area becomes difficult to see due to bleeding. The endscope 1310 is used to obtain a detailed image of the affected area. As this endscope, a flexible endscope which is made of a glass fiber and can be capable bent, a rigid endscope having an optical path made of glass, an electron endscope having an electronic light-receiving portion, etc., should be used. The method of using the solution feed pipe and balloon will be described later.

Figure 22A:
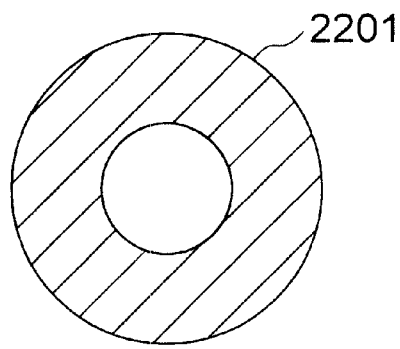
FIGS. 22A to 22D are illustrations of examples of hole of an ultrasonic probe attached to the leading end of a manipulator.
Figure 22B:
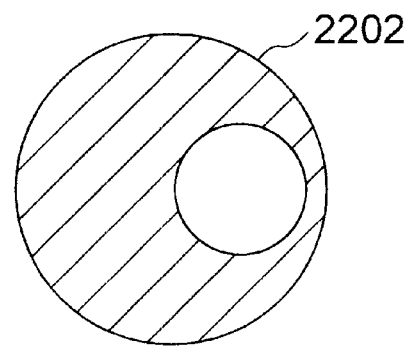
Figure 22C:
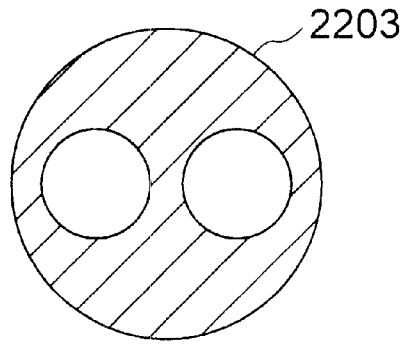
Figure 22D:
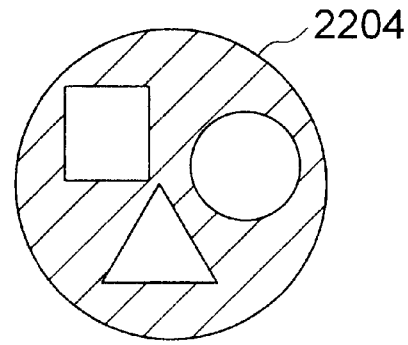

The distal end of the manipulator 1301, water injection pipe 1306, balloon 1307, solution feed pipe 1308, gas feed pipe 1309, and endscope 1310 are threaded into a large number of holes made in one inner cylinder. The cross section of the cylinder is as denoted by the numeral 1311 in FIG. 13F. In this figure, the numeral 1312 denotes a hole through which the water injection pipe 1306 and balloon 1307 shown in FIG. 13B are threaded, the numerals 1312 and 1315 respectively a hole through which the physiological saline solution feed pipe 1308 shown in FIG. 13C is threaded and a hole through which the carbon dioxide gas feed pipe shown in FIG. 13D is threaded, the numerals 1314 and 1316 respectively a hole through which the distal end of manipulator 1301 provided, as shown in FIG. 13A, with any one of the surgical instruments 1302 to 1305 is threaded, and the numeral 1317 a hole through which the endscope 1310 shown in FIG. 13E is threaded. As shown in the lower part of FIG. 13F, this inner cylinder is threaded through an outer cylinder 1318 of manipulator and at the leading end of the outer cylinder, between the outer periphery thereof and the inner periphery of the inner cylinder there is provided an ultrasonic scanner probe 1319. Although in the figure, the inner and outer cylinders are concentrically arranged, this arrangement varies diversely depending on the shape of the probe. The shape of the probe is not limited to a cylinder provided with a hole at the center thereof as indicated by the numeral 2201 in FIG. 22A. For example, the position of the hole may be nearer to one side as shown in FIG. 22B, or there may be a few holes as indicated by the numeral 2203 in FIG. 22C, or the hole shape may be polygonal instead of being circular as indicated by the numeral 2204 in FIG. 22D. Further, the distal end of the inner cylinder itself may be an ultrasonic scanner probe.

Figure 14:
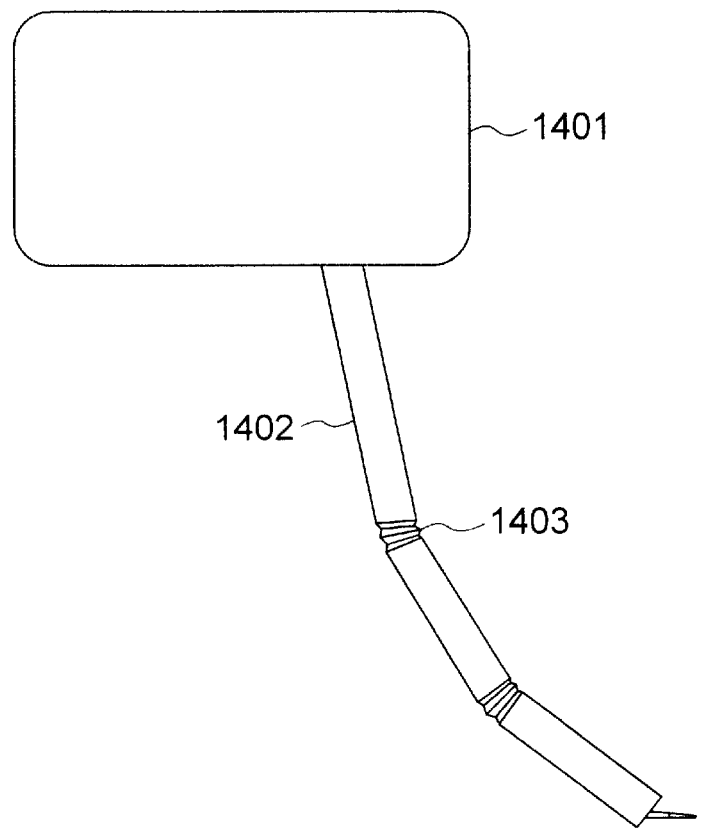
FIG. 14 is a schematic view of the appearance of a manipulator for fine manipulation.

FIG. 14 shows the appearance of a manipulator for fine manipulation. In the figure, the numeral 1401 denotes a drive portion of the manipulator, the numeral 1402 an outer cylinder of the manipulator, and the numeral 1403 a joint of the manipulator.

In a case where an object point faces the leading end of the manipulator, the number of joints 1403 may be 0. However, a point requiring medical treatment may sometimes be hidden behind an organ in question. In this case, it is not seldom that a medical treatment plan which permits a linear approach to the point cannot be necessarily formed because of the presence of an vital tissue at some midpoint and for other reasons. On that occasion, by providing a plurality of joints in the manipulator, it becomes possible for the leading end of the manipulator to move while turning behind, with the result that the region that the distal end of the manipulator can approach expands remarkably.

Incidentally, when a joint is provided, a rigid endscope cannot be used. In this case, therefore, a flexible endscope or an electronic endscope should be used. It is possible to compose or fabricate other elements 1301, 1306 to 1309 from a flexible material.

Figure 15:
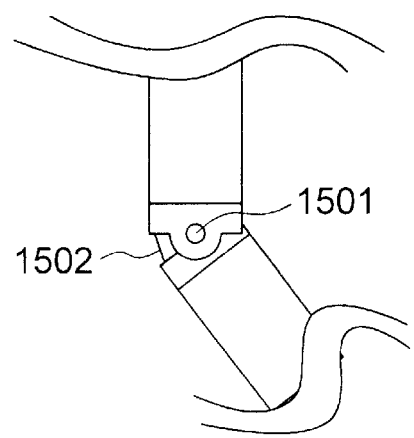
FIG. 15 is a schematic view of an example of construction of a manipulator articulation 1403.

FIG. 15 shows an example of construction of a manipulator joint 1403. In the figure, the numeral 1501 denotes a joint and the numeral 1502 a driving wire.

In the figure, the driving wire 1502 is fixed to a lower link (outer cylinder), passes through an upper link and extends to the drive portion 1401. There is another driving wire on the reverse side of the joint, and each joint is driven by pulling the pair of wires in coordination by means of an actuator (not shown in the figure) present inside the drive portion 1401.

In a case where an organ which is an object of medical treatment is almost stationary like the brain, skelton, etc., medical treatment may be performed by putting a manipulator as described above to full use. However, when the deformation of the organ in question or the movement of the object point occurs due to pulsating movements or respiratory movements as with the heart, lungs, etc., it is necessary to suppress such phenomena.

Examples of construction of a manipulator in a case where the affected organ is flexible and its shape and position change, are described below. As an example of such a case, a bypass operation of the coronary arteries is described here.

Figure 12:
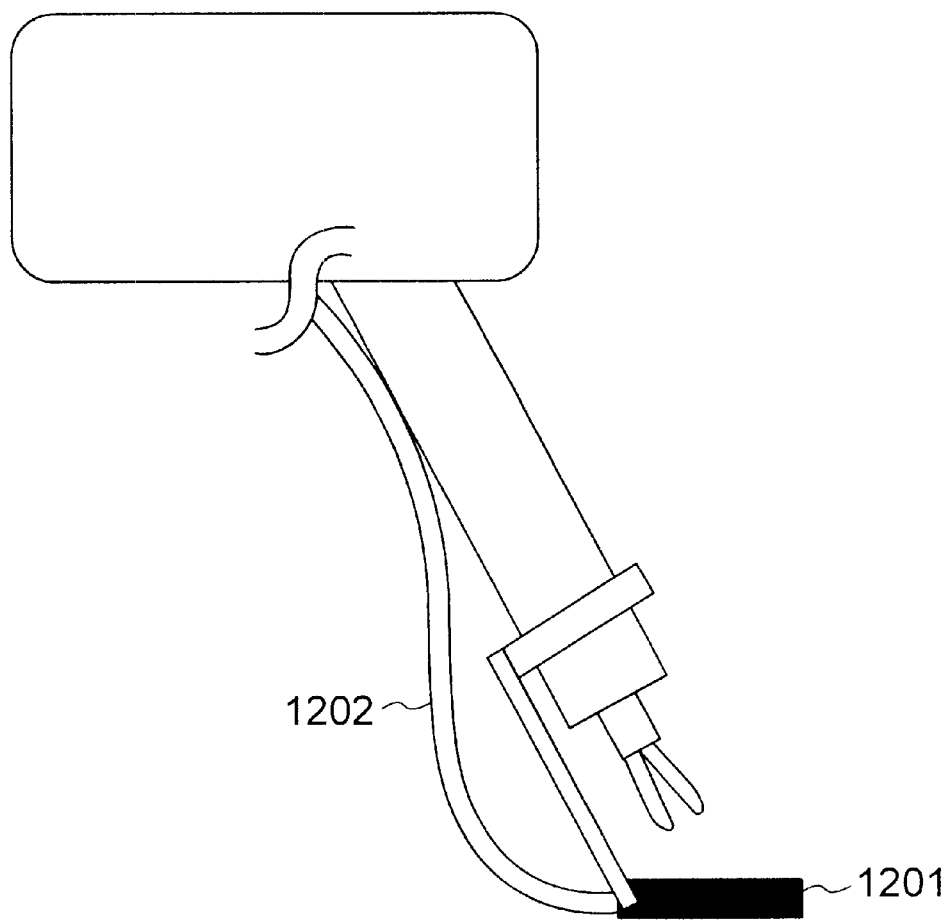
FIG. 12 is a schematic view of affected-area fixing means used in a bypass operation of the coronary arteries.

FIG. 12 shows affected-area fixing means used in a bypass operation of the coronary arteries. In the figure, the numeral 1201 indicates a stabilizer and the numeral 1202 a suction tube.

The stabilizer surface (the surface in contact with a part surrounding the affected area) has a hole and when the air is sucked through the suction tube, the stabilizer surface becomes under negative pressure and attracts the area surrounding the affected area). The stabilizer is fixed to the outer cylinder of a manipulator for fine manipulation. This ensures that in a case where, for example, the object point is a portion present on the surface of the heart, the use of a stabilizer having a shape which surrounds the object point prevents a change in the relative position and posture of the outer cylinder of the manipulator with respect to the object point from occurring even when the absolute position and posture of the object point change due to pulsating movements and respiratory movements. Conventionally, for an internal organ in which the object point moves due to pulsating movements and respiratory movements, it has been very difficult to perform operations such as seaming and anastomosis and such operations have required very high skills even with a maneuverable manipulator having a high position accuracy and resolution. However, such operations are exceedingly lessened with a construction as shown in FIG. 12. Further, as will be describe later, when an endscope is provided inside a manipulator, it is possible to obtain clear stationary images of the object point irrespective of the movement of the internal organ itself, because the object point and the endscope surface are almost stationary relatively to each other.

Further, examples of construction of a stabilizer of a method as shown in FIG. 12 which minimizes the size of an incised portion are explained by the use of FIGS. 16A to 16C, FIGS. 17A to 17C, FIG. 18, and FIGS. 19A to 19D. Incidentally, the outer cylinder of a manipulator is percutaneously inserted and its shape is changed under the skin and, therefore, a space for this purpose is to be ensured.

Figure 16A:
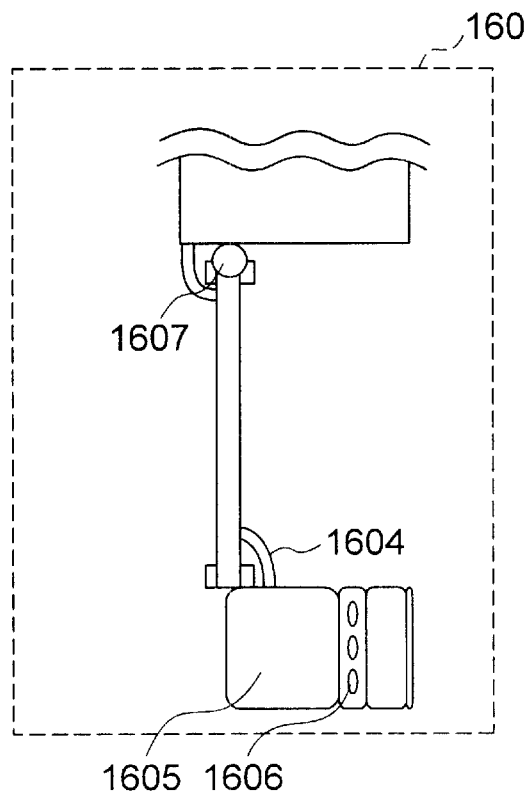
FIG. 16A is a side view of a folding stabilizer attached to the leading end of an outer cylinder of a manipulator.
Figure 16B:
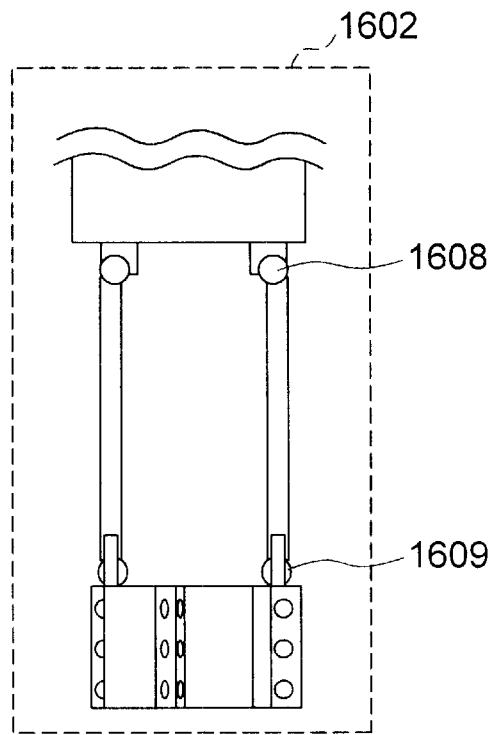
FIG. 16B is a front view of the same folding stabilizer.
Figure 16C:
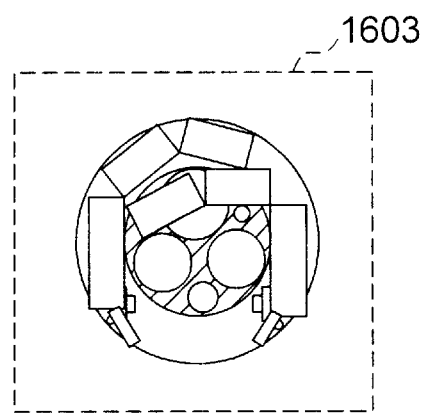
FIG. 16C is a bottom view of the same folding stabilizer.

FIGS. 16A to 16C each show a folding stabilizer attached to the distal end of an outer cylinder of a manipulator. In FIG. 16A the numeral 1601 indicates a side view of the folding stabilizer; in FIG. 16B the numeral 1602 denotes a front view of the same folding stabilizer; and in FIG. 16C the numeral 1603 denotes a bottom view of the same folding stabilizer. In each of FIGS. 16A to 16C, the numeral 1604 denotes a suction tube, the numeral 1605 a suction pad, the numeral 1606 an sucked-air passage, and the numerals 1607 to 1609, respectively, a first joint, a second joint, and a third joint.

The suction tube 1604 passes through the outer cylinder of the manipulator and reaches a compressor provided with a filter (not shown in the figures) by way of a drive portion. Beyond the drive portion, the tube may be threaded through a holding device or may be arranged outside the holding device. A flexible and nonmagnetic material is used as the material for the tube.

The first joint 1607 rotates in an axial direction intersecting at right angles to the face of the paper in 1601, the side view of FIG. 16A. The second joint 1608 rotates around an axis at right angles to the first joint. The third joint 1609 rotates around an axis in the same direction as the second joint. Each joint is provided with a latch mechanism for preventing a reverse rotation (not shown in the figures) and also provided with a stopper to prevent a rotation above a certain angle. In the interior, a torsion spring is installed in order to constantly keep an initial shape. The latch mechanism can be disengaged from the drive portion of the manipulator by means of a transmission mechanism such as a wire. When the latch is in a disengaged condition, each joint moves in a reverse direction due to a torque generated by the torsion screw to thereby return to an initial shape.

The suction bad 1605 includes several parts as shown in 1603, the bottom view of FIG. 16C. The initial shape of the stabilizer is a folded one as shown in FIG. 16A to FIG. 16C and, therefore, the size of an incised portion is sufficient if it allows the outer cylinder of the manipulator to pass through the incised portion, and it is unnecessary to incise a large portion, which might otherwise be required by the installation of a stabilizer.

Figure 17A:
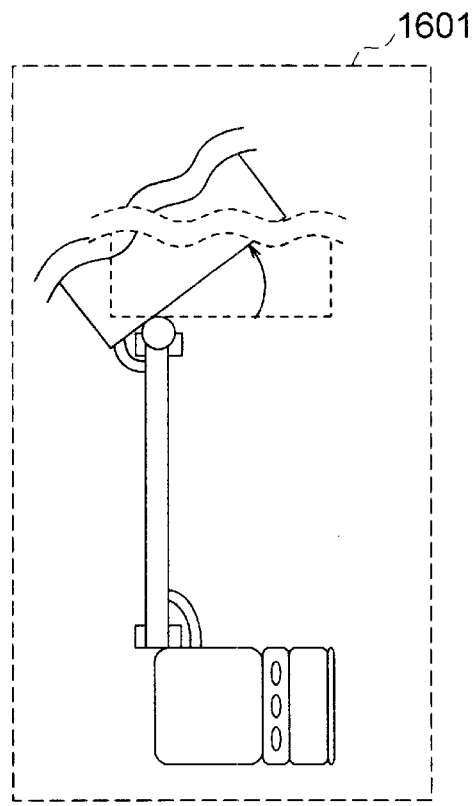
FIG. 17A is an explanatory side view of changes in the movement and shape of each articulation and pad of a folding stabilizer.
Figure 17B:
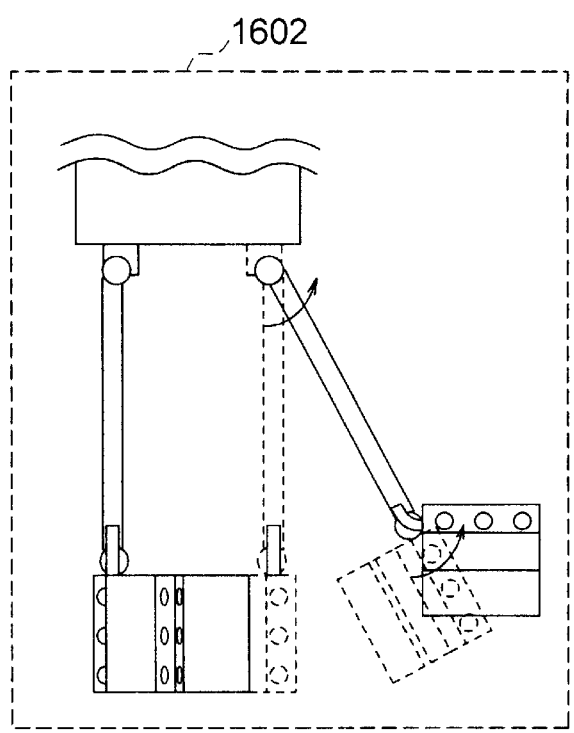
FIG. 17B is an explanatory front view of the same folding stabilizer.
Figure 17C:
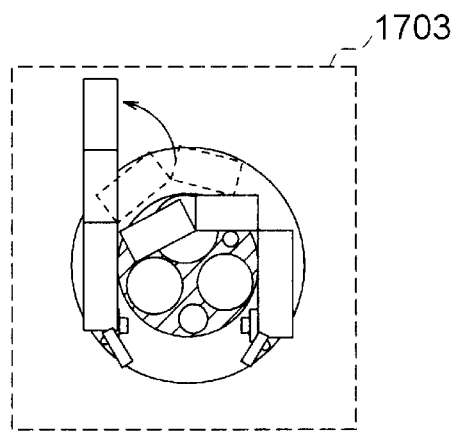
FIG. 17C is an explanatory bottom view of the same folding stabilizer.

FIGS. 17A to 17C show changes in the movement and shape of each joint and pad when the folding stabilizer shown in FIGS. 16A to 16C open and close. FIG. 17A is a side view; FIG. 17B is a front view; and FIG. 17C is a bottom view. The first joint rotates in an axial direction intersecting at right angles to the face of the paper from dotted lines to solid lines as indicated in 1701, the side view of FIG. 17A. The second and third joints each rotate until the pad comes to face a surface that the pad will attract as shown in 1702, the front view of FIG. 17B. The pad can be extended from a folded condition to a straight condition as shown in 1703, the bottom view of FIG. 17C.

Figure 18:
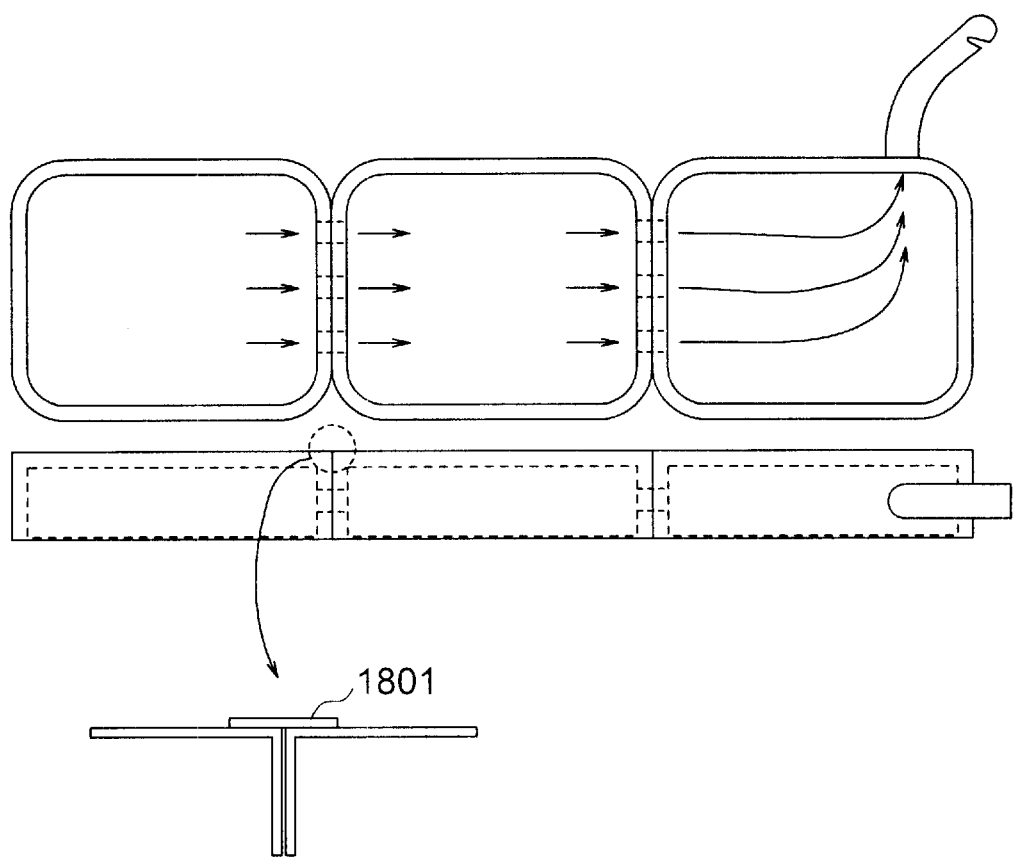
FIG. 18 is an explanatory view of the underside of a pad in an open condition.

FIG. 18 shows the underside of a pad in an open condition. As shown in the figure, the underside of the pad is of a suction-cup structure like the shape of a vessel placed inverted on the surface. When the pad is in a fully-opened condition, the sucked-air passages on the side face of each part become aligned with their corresponding adjacent passages and the air is sucked in as indicated by the arrows when suction from the tube occurs. When the underside is in contact with the surface of the tissue, attraction occurs and the underside is fixed so that the outer cylinder of the manipulator and the object point become stationary with respect to each other due to a force of attraction. At the same time, due to a force of suction each of the parts sucks one another at the sucked-air passages, with the result that the pad is kept in a straight condition. Between the parts there is installed each an elastic hinge 1801 which has the same function as the above torsion spring, and when the stabilizer is in a condition to which an external force is not applied, the bending angle of the hinge is adjusted so as to obtain an initial shape, i.e., a folded shape.

FIGS. 19A to 19D show a sequence adopted when a folding stabilizer is caused to be attracted onto an internal organ in question. As shown in FIG. 19A, the water injection pipe 1306 is first driven by the drive portion of the manipulator so that the water injection pipe 1306 comes and goes out of the hole, and the water injection pipe and balloon 1307 extend from the inner cylinder of the manipulator as indicated by the numeral 1901.

Next, when water is injected into the balloon as indicated by the numeral 1902 in FIG. 19B, balloon bends the second joint 1608 and third joint 1609 while inflating, thereby spreading the pad. Simultaneously, at the root portion thereof the balloon comes into close contact also with the distal end of the manipulator. At this time, the ultrasonic probe 1319 installed at the leading end of the outer cylinder of manipulator is in contact with the internal organ in question via the balloon filled with water. Next, by causing the probe to work, information acquisition by ultrasonic waves is performed. This enables the position of the internal organ in question to be more accurately determined.

On the basis of an ultrasonic scanner image obtained by the above method, fine adjustments of the position and posture of the manipulator are made. After that, as shown in FIG. 19C, the water in the balloon is extracted via the water injection pipe 1306 while the manipulator is caused to be approaching the surface of the internal organ in question. At this point in time, the pad 1605 which has begun to open is now open on the surface of the internal organ by a pressing force. When suction is started, each of the parts of the pad sucks one another due to suction forces as indicated by the numeral 1903, with the result that the pad extends to a maximum degree and is attracted and fixed to the surface of the internal organ.

When the fixed condition has become stable, so as to ensure an approach from a slanting direction as indicated by the numeral 1004 in FIG. 19D, the orientation of the outer cylinder of manipulator is changed while the first joint is caused to be rotating. After that, a manipulator for fine manipulation provided with various kinds of surgical instruments at the leading end thereof extends towards the object point from the holes in the inner cylinder, and fine medical-treatment operations are performed.

Incidentally, the manipulator and the stabilizer may sometimes be independently applied depending on the position and fixed range of an object point. In this case also, it is required that the size of incision for the stabilizer be as minimum as possible. Conventionally, a stabilizer is fixed in such a manner that a portion for holding or attracting the object is bent at right angles to a shaft portion and, therefore, it has been necessary to have an incision which is large to some extent when using the conventional stabilizer.

Figure 20A:
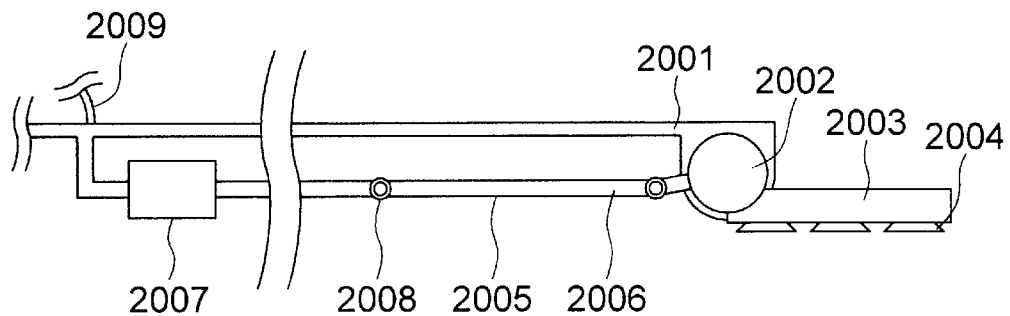
FIGS. 20A and 20B are illustrations of other examples of stabilizer which deforms under the skin.
Figure 20B:
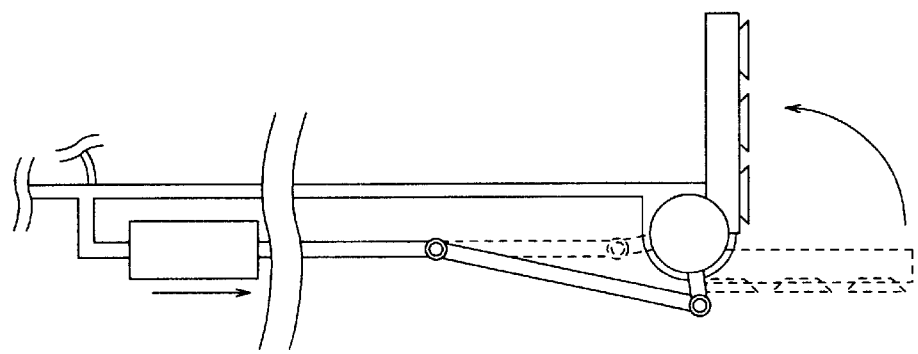

FIGS. 20A and 20B show other examples of stabilizer which deforms under the skin. In FIG. 20A, the numeral 2001 denotes a fixed link, the numeral 2002 a rotary portion, the numeral 2003 a base of attracting portion, the numeral 2004 a suction cup, the numeral 2005 a movable link, the numerals 2006 and 2008 each a pin point, the numeral 2007 an extendable actuator, and the numeral 2009 a suction tube.

The root portion of the fixed link 2001 is fixed to a holding device (not shown in the figure). When a manipulator for fine manipulation is fixed in the same holding device, the positional relationship between the manipulator in question and the stabilizer becomes invariant. Therefore, a tissue fixed by the stabilizer becomes stationary relatively also to the manipulator and the operability by the manipulator improves remarkably.

In using this stabilizer, the base of attracting portion and the movable link are kept in line with each other and the stabilizer is inserted to under the skin from an incision with a small width. After that, by driving the extendable actuator 2007 in a direction of extension, the movable link depresses the end of the rotary portion, thereby rotating the attracting portion, which is integral with the rotary portion as shown in FIG. 20B, from a posture indicated by dotted lines in the lower part of the drawing to a posture indicated by solid lines. This enables the stabilizer to be inserted through a small incised portion and besides, an object tissue (an internal organ) can be positively brought into a stationary condition with respect to the manipulator, which is one of the subjects of operation.

FIG. 21 shows a method of detecting the leading end of a manipulator by MRI and FIGS. 22A to 22D show examples of hole of an ultrasonic probe attached to the distal end of a manipulator. It is needless to say that each element constituting a manipulator, an actuator for driving, an ultrasonic scanner probe, etc., which have been described above, all should be fabricated from nonmagnetic materials that do not sense magnetic fields. The structural members should be fabricated from nonmagnetic metals, such as duralumin and titanium alloys, and engineering plastics. The actuators should be those which are fabricated from nonmagnetic materials alone and which do not work on an electromagnetic principle of driving, for example, ultrasonic motors, hydraulically-driven actuators, pneumatically-driven actuators, etc. The wires should be made of polymeric materials with high toughness. The portions of surgical instruments should be made of ceramics.

Figure 23A:
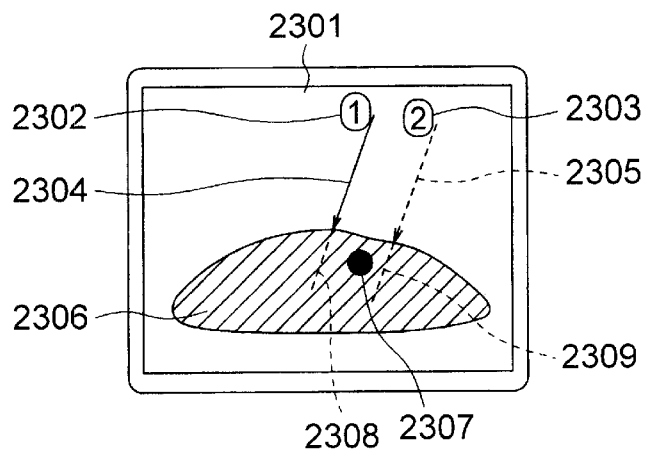
FIGS. 23A to 23C are explanatory views of examples in which it is necessary to perform the sequential modification and updating of a medical treatment plan during an operation through the use of medical treatment planning means.
Figure 23B:
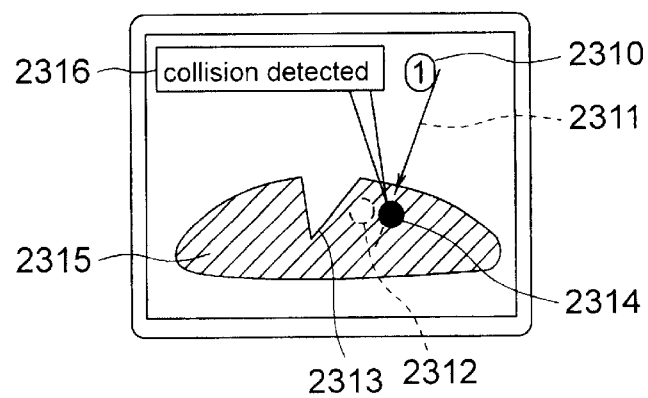
Figure 23C:
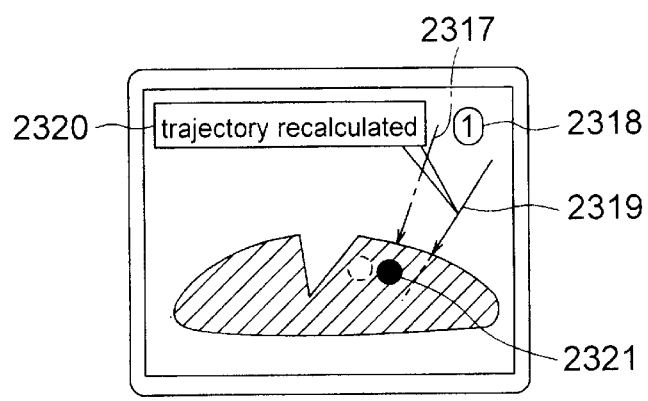

Next, the sequential modification and updating of a medical treatment plan during an operation through the use of medical treatment planning means is explained by FIGS. 23A to 23C. FIG. 23A shows an image in which display means denotes a first condition in a series of procedure; FIG. 23B shows an image in which display means indicates a second condition; and FIG. 23C shows an image in which the display means indicates a third condition. In FIG. 23A, the numeral 2301 denotes a display for presenting images, which is a part of display means, the numeral 2302 a first incision, the numeral 2303 a second incision, the numeral 2304 a scheduled direction of first incision, the numeral 2305 a scheduled direction of second incision, the numeral 2306 an image of the tissue of an object and that near the object, which is obtained by measuring means 101, the numeral 2307 a vital portion that must not be damaged, such as a large blood vessel, the numeral 2308 a contact position in performing the first incision and the depth of the incision, and the numeral 2309 a contact position in performing the second incision and the depth of the incision. In FIG. 23B, the numeral 2310 denotes that after performing the first incision, the schedule for the second incision is pushed forward to the schedule for the first incision, the numeral 2311 a scheduled direction of the first incision, which has been newly pushed forward, the numeral 2312 a position where the vital portion 23 existed before the performance of the first incision in FIG. 23A, the numeral 2313 an incised portion which was generated by the first incision in FIG. 23A, the numeral 2314 a new position of the vital portion 2307 which moved in association with a deformation of tissue caused by the first incision in FIG. 23A, the numeral 2315 an image obtained after the first incision in FIG. 23A, and the numeral 2316 an indication that as a result of the modification and renewal of the medical treatment plan including the newly obtained image, the scheduled direction incision comes into collision with the vital portion if the previous plan is pursued. In FIG. 23C, the numeral 2317 denotes the scheduled direction of incision, which has become null as a result of the modification and renewal of the medical treatment plan, the numeral 2318 an indication that with respect to a scheduled direction of incision, which has been newly calculated, this is the first operation at this point in time, the numeral 2319 a scheduled direction of incision, which has been newly calculated, the numeral 2320 an indication that a scheduled direction of incision has been newly calculated and modified, and the numeral 2321 a schedule position of incision which has been newly calculated.

It is assumed that at a point in time during medical treatment, there is a plan to incise a tissue in two places as shown in FIG. 23A. First, an incise is made according to the scheduled direction of the first incision 2304 and the position and depth of the incision 2308. After the incision, an image is obtained and displayed by the display means 101. Then, when the tissue is soft, it deforms due to its own weight and for other reasons and it is indicated that as shown in FIG. 23B, the vital portion has moved from the position before the first incision 2312 to the position 2314. The new position 2314 is on a line in the schedule direction of second incision on the basis of the plan formed before the deformation of the tissue, and it is indicated to the user by the indication 2316 that the vital portion which has moved would be damaged if an incision is made according to plan. Therefore, the medical treatment means modifies and updates the medical treatment plan on the basis of this information, and then the medical treatment means indicates by the indication 2320 that as shown in FIG. 23C, the scheduled direction of the second incision and the scheduled position and depth of the incision have been moved from 2303 and 2309 of the original plan to 2319 and 2321 of the position which does not damage the vital portion, direction and depth. This enables the medical treatment to be continued while responding to a change in the situation (in this case, a deformation of the tissue). Although this example is very simple, in actuality, however, a very large-scale computation is required in order to quantitatively grasp a deformation of a tissue, etc., and vital portions to be avoided have a very complex distribution. Therefore, a good solution cannot be easily obtained on the basis of decisions made on the spur of the moment. This is the problem of avoidance of an obstacle that, so to speak, dynamically changes, and it is necessary to mathematically solve the above scheduled direction of incision, etc. by putting a high-performance computer to full use.

An image displayed here may be a tomographic image or may be a three-dimensional image reconstructed on the basis of information on a plurality of tomographic images. In the case of a three-dimensional image, a scheduled position of incision is indicated by a line and the direction and depth of incision are indicated by a plane.

Further, according to the circumstances, there is a case where a plan is modified and updated so that a procedure for medical treatment itself is changed. For example, a conceivable case is as follows. That is, as a result of an incision of a point where an anastomosis of blood vessels was planned and also as a result of a palpation, it was found that calcification has proceeded beyond user's expectations and the point of anastomosis must be changed rapidly. In this case, on the basis of information of images taken during the medical treatment, the medical treatment planning means can select a next candidate for a point of anastomosis and present it to the user.

The above essential features of the invention enable information to be obtained by image measuring, etc. during medical treatment. At the same time, on the basis of the accumulation of the image information and vital signs information obtained by measurements, it is possible to modify and update a medical treatment plan according to the condition of a patient and affected area which changes every moment and to carry out medical-treatment operations by holding the size of an incised portion to a minimum even in a case where due to effects of pulsating movements and respiratory movements, a deformation of an internal organ in question and a movement of an object point occur.

In other words, according to the invention, it is possible to realize a medical treatment apparatus which can remarkably improve medical treatment performance. This is because on the basis of the latest information and accumulated information, diagnoses and the generation, modification and updating of a medical treatment plan can be repeatedly carried out during a medical treatment action (during a surgical operation) and, therefore, in order to adapt to the condition of the patient and affected area which change every moment as the medical treatment action proceeds, the best plan at that point in time can be implemented.

As mentioned above, according to the invention, there is provided a medical treatment apparatus which is capable of more exact medical treatment.

What is claimed is:

1. A medical treatment apparatus comprising:
   MRI detection means for detecting positional and functional information as a condition of a human body to be medically treated;
   medical treatment means for treating said human body; and
   display means for displaying results of computing by computing means for computing a plan for said medical treatment based on the positional and functional information detected by said MRI detection means;
   wherein said display means displays a range in which said medical treatment means can move on the basis of said results of computing.

2. A medical treatment apparatus according to claim 1, further comprising control means for regulating the movement of said medical treatment means on the basis of said results of computing.

3. A medical treatment apparatus according to claim 1, further comprising control means for regulating the orientation of said medical treatment means on the basis of said results of computing.

4. A medical treatment apparatus according to any one of claims 1 to 3, further comprising means for displaying changes in the plan on the basis of said results of computing.

5. A medical treatment apparatus according to claim 1, wherein the medical treatment means treats the human body using surgical instruments which physically contact the human body.

6. A medical treatment apparatus comprising:
   MRI detection means for detecting positional and functional information as a condition of a human body to be medically treated;
   medical treatment means for medically treating the human body by remote control;
   computing means for determining a medical treatment plan for medical treatment of the human body based on the positional and functional information detected by the MRI detection means;
   control means for remote-controlling the medical treatment means based on the medical treatment plan determined by the computing means to carry out the medical treatment plan determined by the computing means; and
   display means for displaying results obtained by the computing means.

7. A medical treatment apparatus according to claim 6, wherein the medical treatment means includes a manipulator having a tip end, medical treatment instruments being mountable on the tip end of the manipulator; and
   wherein the control means controls a movement of the manipulator.

8. A medical treatment apparatus according to claim 6, wherein the medical treatment means includes a manipulator having a tip end, medical treatment instruments being mountable on the tip end of the manipulator; and
   wherein the control means controls an orientation of the manipulator.

9. A medical treatment apparatus according to claim 6, further comprising memory means for storing a medical treatment plan in advance;
   wherein when the medical treatment plan determined by the computing means differs from the medical treatment plan stored in the memory means, the display means displays changes in the medical treatment plan stored in the memory means based on the medical treatment plan determined by the computing means.

10. A medical treatment apparatus according to any one of claims 6 to 9, wherein the display means displays an operation range of the medical treatment means.

11. A medical treatment apparatus according to claim 6, wherein the MRI detection means periodically detects the positional and functional information while the control means is remote-controlling the medical treatment means based on the medical treatment plan determined by the computing means to carry out the medical treatment plan determined by the computing means; and
   wherein the computing means periodically updates the medical treatment plan determined by the computing means while the control means is remote-controlling the medical treatment means based on the medical treatment plan determined by the computing means to carry out the medical treatment plan determined by the computing means based on the functional and positional information periodically detected by the MRI detection means.

12. A medical treatment apparatus according to claim 6, wherein the medical treatment means treats the human body using surgical instruments which physically contact the human body.

* * * * *